United States Patent [19]
Oshlack et al.

[11] Patent Number: 5,472,712
[45] Date of Patent: * Dec. 5, 1995

[54] CONTROLLED-RELEASE FORMULATIONS COATED WITH AQUEOUS DISPERSIONS OF ETHYLCELLULOSE

[75] Inventors: Benjamin Oshlack, New York, N.Y.; Mark Chasin, Manalpan, N.J.; Frank Pedi, Jr., Yorktown Heights, N.Y.

[73] Assignee: Euroceltique, S.A., Luxembourg

[*] Notice: The portion of the term of this patent subsequent to Dec. 28, 2010, has been disclaimed.

[21] Appl. No.: 81,618

[22] Filed: Jun. 23, 1993

Related U.S. Application Data

[63] Continuation-in-part of Ser. No. 814,111, Dec. 24, 1991, Pat. No. 5,273,760.

[51] Int. Cl.$^6$ ............................... A61K 9/14; A61K 9/16; A61K 9/36; A61K 9/62
[52] U.S. Cl. .................... 424/480; 424/461; 424/495; 424/408; 424/418; 514/772.1; 514/781; 427/2.16; 427/213.31; 427/372.2; 427/377; 71/64.07; 71/64.13
[58] Field of Search .................... 424/480, 495; 514/772.1, 781; 427/3, 213.31, 372.2, 377; 428/407

[56] References Cited

U.S. PATENT DOCUMENTS

| | | | |
|---|---|---|---|
| 3,567,650 | 3/1971 | Bakan | 252/316 |
| 3,870,790 | 3/1975 | Lowey et al. | 424/19 |
| 4,138,475 | 2/1979 | McAinsh et al. | 424/19 |
| 4,377,568 | 3/1983 | Chopra | 424/31 |
| 4,385,078 | 5/1983 | Onda et al. | 427/3 |
| 4,443,497 | 4/1984 | Samejima et al. | 427/213.36 |
| 4,600,645 | 7/1986 | Ghebre-Sellasie et al. | 428/403 |
| 4,756,911 | 7/1988 | Drost et al. | 424/468 |
| 4,766,012 | 8/1988 | Valenti | 427/213.36 |
| 4,784,858 | 11/1988 | Ventouras | 424/468 |

(List continued on next page.)

FOREIGN PATENT DOCUMENTS

| | | |
|---|---|---|
| 0166608 | 8/1985 | Japan . |
| 2170104 | 7/1986 | United Kingdom . |

OTHER PUBLICATIONS

D. L. Munday, A. R. Fassihi, 5th Congr. Int. Tech. Pharm. vol. 2, pp. 55–60 Changes in Drug Release Rate, Effect of Temperature and Relative Humidity on Polymeric Film Coating, 1989, Assoc. Pharm. Galenique Ind., Chatenay Malabry, FR.

J. B. Dressman, C. Jarvis, A. G. Ozturk, B. O. Palsson, and T. A. Wheatley 18th Int. Symposium on Controlled Release Of Bioactive Materials pp. 654–655, "Storage Effects on Release From Phenylpropanolamine HCl Pellets Coated With an Ethylcellulose–based Film", 1991, Amsterdam, Netherlands, Pub. by the Controlled Release Society, Inc.

*Primary Examiner*—Edward J. Webman
*Attorney, Agent, or Firm*—Steinberg, Raskin & Davidson

[57] ABSTRACT

A stabilized solid controlled release formulation having a coating derived from an aqueous dispersion of a hydrophobic polymer is obtained by overcoating a substrate including an active agent selected from the group consisting of a systemically active therapeutic agent, a locally active therapeutic agent, a disinfecting and sanitizing agent, a cleansing agent, a fragrance agent and a fertilizing agent, with an aqueous dispersion of the plasticized hydrophobic polymer and then curing the coated substrate at a temperature above the glass transition temperature of the plasticized hydrophobic polymer, until a curing endpoint is reached at which the coated substrate provides a stabilized dissolution of the active agent which is unchanged after exposure to accelerated storage conditions, the endpoint being determined by comparing the dissolution profile of the formulation immediately after curing to the dissolution profile of the formulation after exposure to accelerated storage conditions of at least one month at a temperature of 37° C. and at a relative humidity of 80%.

118 Claims, 18 Drawing Sheets

U.S. PATENT DOCUMENTS

| | | | |
|---|---|---|---|
| 4,786,505 | 11/1988 | Lovgren et al. | 424/468 |
| 4,786,506 | 11/1988 | Fontanelli | 424/470 |
| 4,795,327 | 1/1989 | Gaylord et al. | 424/468 |
| 4,810,501 | 3/1989 | Ghebre-Sellasie et al. | 424/469 |
| 4,837,004 | 6/1989 | Wu et al. | 424/438 |
| 4,837,033 | 6/1989 | Kokubo et al. | 424/494 |
| 4,849,229 | 7/1989 | Gaylord et al. | 424/468 |
| 4,853,230 | 8/1989 | Lovgren et al. | 424/466 |
| 4,954,350 | 9/1990 | Jones et al. | 424/493 |
| 4,983,730 | 1/1991 | Domeshek et al. | 536/69 |
| 5,008,118 | 4/1991 | Iwanmi et al. | 424/498 |
| 5,009,897 | 4/1991 | Brinker et al. | 424/469 |
| 5,042,842 | 6/1991 | Edgren et al. | 424/473 |
| 5,047,258 | 9/1991 | Belanger et al. | 427/3 |
| 5,064,650 | 11/1991 | Lew | 424/435 |
| 5,068,110 | 11/1991 | Fawzi et al. | 424/461 |
| 5,077,053 | 12/1991 | Kuncewitch et al. | 424/441 |
| 5,084,278 | 1/1992 | Mehta | 424/441 |
| 5,085,866 | 2/1992 | Cowsar et al. | 424/481 |
| 5,091,175 | 2/1992 | Imondi et al. | 424/486 |
| 5,096,717 | 3/1992 | Wirth et al. | 424/490 |
| 5,112,384 | 6/1992 | Paradissis et al. | 424/451 |
| 5,112,621 | 5/1992 | Stevens et al. | 424/497 |
| 5,133,974 | 7/1992 | Paradissis et al. | 424/480 |
| 5,158,777 | 10/1992 | Abramowitz et al. | 424/458 |
| 5,160,742 | 11/1992 | Mazer et al. | 424/469 |
| 5,171,580 | 12/1992 | Iamartino et al. | 424/490 |
| 5,178,866 | 1/1993 | Wright et al. | 424/473 |
| 5,186,937 | 2/1993 | Sparks et al. | 424/438 |
| 5,202,128 | 4/1993 | Morella et al. | 424/469 |
| 5,213,811 | 5/1983 | Friskee et al. | 424/493 |
| 5,219,621 | 6/1993 | Geoghegan et al. | 424/462 |

CONTROLLED-RELEASE FORMULATIONS COATED WITH AQUEOUS DISPERSIONS OF ETHYLCELLULOSE

This application is a continuation-in-part of U.S. application Ser. No. 07/814,111 filed Dec. 24, 1991, now U.S. Pat. No. 5,273,760, issued Dec. 28, 1993.

BACKGROUND OF THE INVENTION

An important aspect of the manufacture, regulatory review and approval of all dosage forms concerns their stability over extended periods of time. The stability data obtained with regard to a particular dosage form directly affects its shelf-life. The stability of a pharmaceutical dosage form is related to maintaining its physical, chemical, microbiological, therapeutic, and toxicological properties when stored, i.e., in a particular container and environment. Stability study requirements are covered, e.g., in the Good Manufacturing Practices (GMPs), the U.S.P., as well as in the regulatory requirements of the country where approval to market a dosage form is being sought. In the United States, a request to test, and eventually market, a drug or a drug formulation may be made via a New Drug Application (NDA), an Abbreviated New Drug Application (ANDA) or an Investigational New Drug Applications (IND).

The agents used in sustained release dosage formulations often present special problems with regard to their physical stability during storage. For example, waxes which have been used in such formulations are known to undergo physical alterations on prolonged standing, thus precautions are taken to stabilize them at the time of manufacture or to prevent the change from occurring. Fats and waxy materials when used in purified states are known to crystallize in unstable forms, causing unpredictable variations in availability rates during stability testing at the time of manufacture and during later storage.

It is known that certain strategies can be undertaken to obtain stabilized controlled release formulations in many cases, such as insuring that the individual agents are in a stable form before they are incorporated into the product, and that processing does not change this condition, retarding the instability by including additional additives, and inducing the individual agents of the dosage form to reach a stable state before the product is finally completed.

It is also recognized that the moisture content of the product can also influence the stability of the product. Changes in the hydration level of a polymeric film, such as the ethyl celluloses, can alter the rate of water permeation and drug availability. Also, binders such as acacia are known to become less soluble when exposed to moisture and heat. However, moisture content of a product can be controlled fairly successfully by controls in the processing method and proper packaging of the product.

Hydrophobic polymers such as certain cellulose derivatives, zein, acrylic resins, waxes, higher aliphatic alcohols, and polylactic and polyglycolic acids have been used in the prior art to develop controlled release dosage forms. Methods of using these polymers to develop controlled release dosage forms such as tablets, capsules, suppositories, spheroids, beads or microspheres are to overcoat the individual dosage units with these hydrophobic polymers. It is known in the prior art that these hydrophobic coatings can be applied either from a solution, suspension or dry. Since most of these polymers have a low solubility in water, they are usually applied by dissolving the polymer in an organic solvent and spraying the solution onto the individual drug forms (such as beads or tablets) and evaporating off the solvent.

Aqueous dispersions of hydrophobic polymers have been used in the prior art to coat pharmaceutical dosage forms for aesthetic reasons such as film coating tablets or beads or for taste-masking. However, these dosage forms are used for immediate release administration of the active drug contained in the dosage form.

The use of organic solvents in the preparation of hydrophobic coatings is considered undesirable because of inherent problems with regard to flammability, carcinogenicity, environmental concerns, and safety in general. It considered very desirable in the art, however, to provide a controlled release coating derived from aqueous dispersions of a hydrophobic material, such as ethyl cellulose.

Unfortunately, to date, while many formulations have been experimentally prepared which rely upon a hydrophobic coating derived from an aqueous dispersion to provide controlled release of an active agent, such formulations have not proven to be commercially viable because of stability problems. Aqueous polymeric dispersions have been used to produce stable controlled release dosage forms, but this has only been possible by other methods such as incorporation of the same into the matrix of the dosage form, rather than via the use of a coating of the aqueous polymeric dispersion to obtain retardant properties.

When coating using aqueous polymeric dispersions to obtain a desired release profile of the active agent(s) over several hours or longer, it is known in the art that the dissolution release profile changes on ageing, e.g. when the final coated product is stored for a period of time, during which time it may be exposed to elevated temperature and/or humidity above ambient conditions. This problem is illustrated, for example, by Dressman, et al., Proceed. Intern. Symp. Control. Rel. Bioact. Mater., 18 (1991), pp. 654–655, Controlled Release Society, Inc. who reported that phenylpropanolamine HCl pellets coated with an ethyl cellulose-based film are only stable at room temperature under ambient humidity conditions. Munday, et al., Drug Devel. and Indus. Phar., 17 (15) 2135–2143 (1991) similarly reported that film coated theophylline mini-tablets film coated with ethyl cellulose with PEG (2:1), and ethyl cellulose with Eudragit L (2:1) impeded dissolution upon storage under stress conditions, the degree of slowdown of release being said to be directly proportional to temperature, while the effect of relative humidity (RH) appeared to be insignificant. Munday, et al. concluded that the decreased rate of release was due to the slowing in the rate of molecular diffusion of the drug across the polymeric coating material, and suggested that the change was due to significant alterations in the permeability of the polymer which occurred during the experimental storage.

This instability problem is known to not exist when the polymers are applied from organic solvent solution.

OBJECTS AND SUMMARY OF THE INVENTION

It is therefore an object of the present invention to provide a controlled release tablet comprising a core containing an active agent, e.g. a therapeutically active agent, a disinfecting agent, a cleansing agent, a sanitizing agent and a fertilizing agent coated with an aqueous dispersion of a hydrophobic polymer, e.g. alkylcellulose or acrylic polymers such that there is a stable dissolution profile of the active agent when placed in an environment of use.

It is another object of the present invention to provide a controlled release formulation comprising a plurality of inert beads comprising an effective amount of an active agent, the beads being coated with an aqueous dispersion of a hydrophobic polymer and providing a reproducible, stable dissolution despite exposure to accelerated storage conditions.

It is another object of the present invention to provide a method of preparing a controlled release tablet comprising a core containing an active agent coated with an aqueous dispersion of a hydrophobic polymer such that there is a stable dissolution profile of the active agent when placed in an environment of use, despite exposure to accelerated storage conditions.

Still another object of the present invention is to provide a controlled release formulation comprising a substrate containing an active agent coated with an aqueous dispersion of a hydrophobic polymer such that there is a stable dissolution profile of the active agent when placed in an environment of use, even after storage for a period of time where the coated formulation may be exposed to storage conditions of temperature and/or humidity elevated above ambient conditions.

A further object of the present invention is to provide a controlled release formulation wherein the controlled release is caused by a coating on the formulation of an aqueous dispersion of a hydrophobic polymer such as ethylcellulose which coating provides a stable dissolution of an active agent contained in the formulation, despite exposure to accelerated storage conditions such that the dissolution would be deemed acceptable by a governmental regulatory agency such as the U.S. FDA for purposes of according expiration dating.

The above-mentioned objects and others are accomplished by the present invention, which relates in part to a controlled release formulation comprising a substrate containing an active agent in an amount sufficient to provide a desired effect in an environment of use, said substrate coated with an aqueous dispersion of plasticized ethylcellulose in an amount sufficient to obtain a controlled release of said active agent when said formulation is exposed to an environmental fluid. The coated substrate is cured at a temperature greater than the glass transition temperature of the aqueous dispersion of plasticized ethylcellulose and at a relative humidity from about 60% to about 100% for a sufficient period of time until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions, e.g., of one-three months at a temperature of 37° C. and at a relative humidity of 80%. In certain preferred embodiments, the substrate is coated to a weight gain from about 2% to about 25%.

In other embodiments, the coated substrate is cured at a temperature greater than the glass transition temperature of the aqueous dispersion of plasticized ethylcellulose and at a relative humidity from about 60% to about 100% to cause individual ethylcellulose particles in said coating to coalesce and to gradually slow the release of said active agent when exposed to an environmental fluid, until an endpoint is reached at which the cured coated substrate, when subjected to in-vitro dissolution, releases said active agent in amounts which do not vary at any time point along the dissolution curve by more than about 20% of the total amount of active agent released, when compared to the in-vitro dissolution of said coated substrate prior to curing.

In yet other embodiments of the invention, the cured formulation provides a stabilized dissolution of said active agent which is unchanged after exposure to accelerated storage conditions, the stabilized dissolution being deemed appropriate by the United States Food & Drug Administration for the purpose of according expiration dating for said formulation.

Other preferred embodiments relate to controlled release dosage formulation comprising a substrate coated with an effective amount of an aqueous dispersion of ethylcellulose to obtain a controlled release of an active agent which formulation, after exposure to accelerated storage conditions of at least one month at 40° C./75% RH, releases an amount of therapeutically active agent which does not vary at any given dissolution time point by more than about 20% of the total amount of therapeutically active agent released, when compared to in-vitro dissolution conducted prior to storage.

In other embodiments, the coated substrate, upon in-vitro dissolution testing, provides a band range after exposure to accelerated storage conditions which is not wider than about 20% at any point of time when compared to the dissolution profile prior to exposure to the accelerated storage conditions.

The active agent may be chosen for a wide variety of uses, including but not limited to systemically active therapeutic agents, locally active therapeutic agents, disinfectants, cleansing agents, fragrances, fertilizers, deodorants, dyes, animal repellents, insect repellents, pesticides, herbicides, fungicides, and plant growth stimulants.

The present invention is further related to a solid controlled release oral dosage formulation, comprising a substrate containing an systemically active therapeutic agent in an amount sufficient to provide a desired therapeutic effect when said formulation is orally administered. The substrate is coated with an aqueous dispersion of plasticized ethylcellulose and cured at a temperature greater than the glass transition temperature of the aqueous dispersion of plasticized ethylcellulose and at a relative humidity from about 60% to about 100% for a period of time sufficient to obtain a controlled release of said active agent when measured by the USP Paddle Method at 100 rpm at 900 ml aqueous buffer (pH between 1.6 and 7.2) at 37° C. from about 5% to about 42.5% (by wt) active agent released after 1 hour, from about 15% to about 60% (by wt) active agent released after 2 hours, from about 17% to about 75% (by wt) active agent released after 4 hours, and from about 20% to about 90% (by wt) active agent released after 8 hours, said coated substrate being cured to cause individual ethylcellulose particles in said coating to coalesce and to gradually slow the release of said active agent when exposed to an environmental fluid until an endpoint is reached at which the release rate (e.g., invitro dissolution) obtained after exposing the cured, coated substrate to accelerated storage conditions of 37° C. and 80% relative humidity for one-three months is stable when compared to the release rate obtained immediately after curing. The dosage form preferably provides a therapeutic effect for about 24 hours. The present invention further relates to a method of preparing the dosage form.

The present invention is also related to a method for obtaining a controlled release formulation of an active agent, comprising preparing a solid substrate comprising an active agent, coating the substrate with a sufficient amount of an aqueous dispersion of plasticized ethylcellulose to obtain a predetermined controlled release of the active agent when the coated substrate is exposed to an environmental fluid, and curing the coated substrate at a temperature greater than the glass transition temperature of the aqueous dispersion of plasticized ethylcellulose and at a relative humidity from about 60% to about 100% until a curing endpoint is reached at which said coated substrate provides a stabilized dissolution of said active agent which is unchanged after exposure to accelerated storage conditions. The endpoint is determined, e.g., by comparing the dissolution profile of the formulation immediately after curing to the dissolution profile of the formulation after exposure to accelerated storage conditions of, for example, one-three months at a temperature of 37° C. and at a relative humidity of 80%.

The present invention is further related to a method of treating a patient with an oral solid dosage form described above. In this method, present invention further comprises administering the oral solid dosage form comprising the cured, coated substrate to the patient to thereby obtain the desired therapeutic effect for about 12 to about 24 hours. In especially preferred embodiments, the oral solid dosage forms of the present invention provide a desired therapeutic effect for about 24 hours.

The present invention provides many benefits over prior art coatings, including, but not limited to, avoidance of organic solvents which have inherent safety concerns (flammability, carcinogenicity, environmental concerns, safety in general), and extended stability which may result in extended shelf life and expiration dating.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
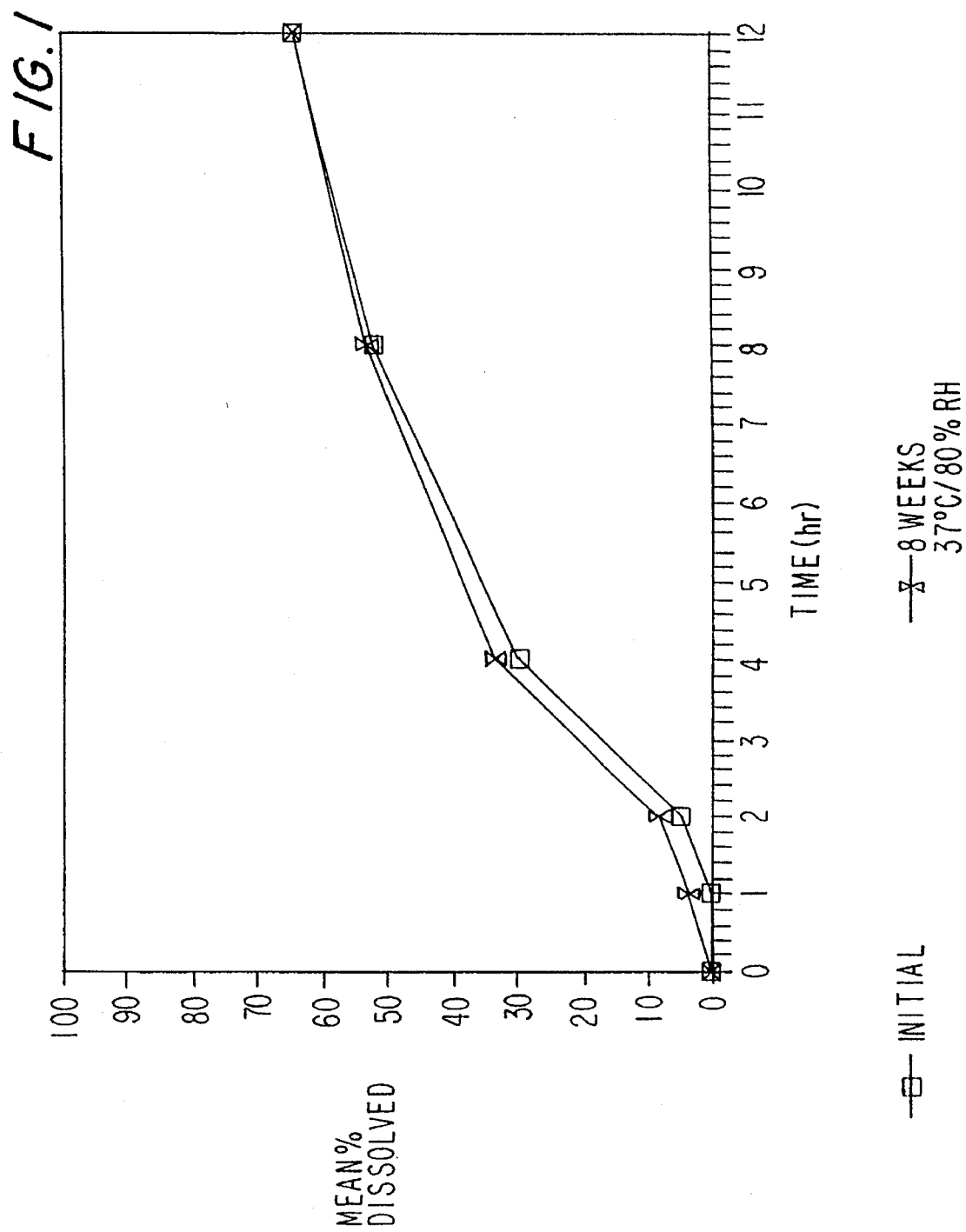
FIG. 1 is a graphical representation of the dissolution stability results obtained with Example 1.

The aqueous dispersions of hydrophobic polymers used as coatings in the present invention may be used to coat substrates such as tablets, spheroids (or beads), microspheres, seeds, pellets, ion-exchange resin beads, and other multi-particulate systems in order to obtain a desired controlled release of the active agent. Granules, spheroids, or pellets, etc., prepared in accordance with the present invention can be presented in a capsule or in any other suitable dosage form. The tablets of the present invention may be any suitable shape, such as round, oval, biconcave, hemispherical, any polygonal shape such as square, rectangular, and pentagonal, and the like.

In order to obtain a controlled release formulation, it is usually necessary to overcoat the substrate comprising the active agent with a sufficient amount of the aqueous dispersion of hydrophobic polymer e.g., ethylcellulose, to obtain a weight gain level from about 2 to about 25 percent, although the overcoat may be lesser or greater depending upon the physical properties of the active agent and the desired release rate, the inclusion of plasticizer in the aqueous dispersion and the manner of incorporation of the same, for example.

The cured, coated substrates of the present invention provide a stable dissolution profile (e.g., release of the active agent in the environment of use) when stored for extended periods of time at room temperature and ambient humidity (e.g., long term (real time) testing), and when tested under accelerated storage conditions.

The terms "stable dissolution profile" and "curing endpoint" are defined for purposes of the present invention as meaning that the cured, coated substrate reproducibly provides a release of the active agent when placed in an environment of use which is unchanged, even after exposing the cured, coated substrate to accelerated storage conditions. Those skilled in the art will recognize that by "unchanged" it is meant that any change in the release of the active agent from the cured, coated formulation would be deemed insignificant in terms of the desired effect. For pharmaceutical formulations, stability is determined by, e.g, a regulatory agency such as the Food & Drug Administration (FDA) in the U.S., for the purpose of according an expiration date for the formulation.

By the phrase "accelerated storage conditions" it is meant, e.g., storage conditions of elevated temperature and/or elevated relative humidity. Preferably, the phrase "accelerated storage conditions" refers to storage conditions to which the final drug formulation is subjected for the purpose of obtaining regulatory approval (e.g., FDA approval in the U.S.) and an expiration date.

The term "expiration date" is defined for purposes of the present invention as the date designating the time during which a batch of the product (e.g., the cured, coated substrate) is expected to remain within specification if stored under defined conditions, and after which it should not be used.

The term "band range" for purposes of the present invention is defined as the difference in in-vitro dissolution measurements of the controlled release formulations when comparing the dissolution profile (curve) obtained by the formulation upon completion of the manufacturing of the coated product (prior to storage) and the dissolution profile obtained after the coated product is exposed to accelerated storage conditions, expressed as the change in percent of the active agent released from the coated product at any dissolution time point along the dissolution curves.

In general, the length of the studies and the storage test conditions required by regulatory agencies such as the FDA for pharmaceutical formulations are sufficient to cover storage, shipment, and subsequent use. Allowable storage test conditions may vary depending upon the particulars of the product. For example, temperature sensitive drug substances should be stored under an alternative, lower temperature condition, which is then deemed to be the long term testing storage temperature. In such cases, it is generally accepted that the accelerated testing should be carried out at a temperature at least 15° C. above this designated long term storage temperature, together with appropriate relative humidity conditions for that temperature.

A generally accepted accelerated test employed in FDA guidelines relates to the storage of a drug product (e.g., in its container and package) at 80% Relative Humidity (RH) and 37° C. (1985 FDA guidelines). If the product holds up for, e.g., three months under these conditions (chemical stability, dissolution, and physical characteristics), then the drug product will be accorded, e.g., a two year expiration date. This accelerated test is also now also considered to be acceptable if conducted at 75% RH and 40° C. (FDA 1987 guidelines). It has recently been proposed that long-term storage testing be conducted for pharmaceutical formulations at 25° C.±2° C. at not less than 60% RH ±5% for a minimum time period of 12 months. It has been further proposed that accelerated testing be conducted for pharmaceutical formulations at 40° C.±2° C. at 75% RH ±5% for a minimum time period of 6 months. All of the above-mentioned accelerated testing criteria and others are deemed equivalent for purposes of the present invention, with regard to the determination of stability and the determination of the curing endpoint.

The controlled release coatings of the present invention comprise aqueous dispersions of hydrophobic polymers. Although ethylcellulose is an especially preferred hydrophobic polymer for use in the controlled release coatings of the present invention, other hydrophobic cellulosic derivatives (including other alkyl celluloses) may be also be used, and are deemed to be encompassed by the appended claims.

The inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material.

The plasticization of the ethylcellulose may be accomplished either by so-called "internal plasticization" and "external plasticization." The suitability of a plasticizer depends on its affinity or solvating power for the polymer and its effectiveness at interfering with polymer-polymer attachments. Such activity imparts the desired flexibility by relieving molecular rigidity. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

An important parameter in the determination of a suitable plasticizer for a polymer is related to the glass transition temperature (Tg) of the polymer. The glass transition temperature is related to the temperature or temperature range where there is a fundamental change in the physical properties of the polymer. This change does not reflect a change in state, but rather a change in the macromolecular mobility of the polymer.

Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that under ambient conditions the films are softer, more pliable and often stronger, and thus better able to resist mechanical stress.

Other aspects of suitable plasticizers include the ability of the plasticizer to act as a good "swelling agent" for the ethylcellulose, and the insolubility of the plasticizer in water.

Examples of suitable plasticizers for the hydrophobic polymers useful in the present invention (e.g., ethylcellulose) include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

In one commercially available product, Aquacoat® (aqueous dispersion of ethylcellulose available from FMC Corp., Philadelphia, Pa., U.S.A.), the ethylcellulose is dissolved in a water-immiscible organic solvent and then emulsified in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use. Another aqueous dispersion of ethylcellulose is commercially available as Surelease® (Colorcon, Inc., West Point, Pennsylvania, U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

With respect to handling and storage conditions, FMC states that Aquacoat® will undergo a rise in viscosity upon prolonged exposure to temperatures below 15° C. or above 35° C., and that viscosity can be reduced to less than 100 cps by applying shear (e.g., propeller type mixer). FMC further states that a continuous film may be formed through a process known as gradual coalescence wherein the individual latex particles coalesce to form a continuous film of plasticized ethylcellulose polymer. After this period, the properties are said to remain constant. Higher coating temperatures, or a high temperature "curing" step is said by FMC to accelerate the process. If the coalescence process is not complete, FMC states that variability in release rates will result.

The stabilized controlled release formulations of the present invention slowly release the active agent, e.g., when placed in an environmental fluid in an environment of use. By "environmental fluid", it is meant that the formulation is placed in an aqueous solution (e.g., in-vitro dissolution), in simulated gastric fluid (e.g., in accordance with the USP Basket Method (i.e., 37° C., 100 RPM, first hour 700 ml gastric fluid at pH 1.2, then changed to 900 ml at pH 7.5), or in gastrointestinal fluid (in-vivo).

The controlled release profile of the formulations of the invention can be altered, for example, by varying the amount of overcoating with the aqueous dispersion of hydrophobic polymer, altering the manner in which the plasticizer is added to the aqueous dispersion of hydrophobic polymer, by varying the amount of plasticizer relative to hydrophobic polymer, by the inclusion of additional agents or excipients, by altering the method of manufacture, etc.

In one preferred embodiment of the present invention, the controlled release dosage form comprises pharmaceutically acceptable beads (e.g., spheroids) containing the active ingredient coated with a controlled release coating. The term spheroid is known in the pharmaceutical art and means, e.g., a spherical granule having a diameter of between 0.2 mm and 2.5 mm especially between 0.5 mm and 2 mm. A suitable commercially available example of such beads are nu pariel 18/20 beads.

A plurality of the cured, coated (stabilized) controlled release spheroids may thereafter be placed in a gelatin capsule in an amount sufficient to provide an effective controlled release dose when ingested and contacted by gastric fluid.

Spheroids or beads coated with a therapeutically active agent are prepared, e.g. by dissolving the therapeutically active agent in water and then spraying the solution onto a substrate, for example, nu pariel 18/20 beads, using a Wurster insert. Optionally, additional agents are also added prior to coating the beads in order to assist the hydromorphone binding to the beads, and/or to color the solution, and the like. For example, a product which includes hydroxypropyl methylcellulose, and the like with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropyl methylcellulose (HPMC). However, any film-former known in the art may be used. It is preferred that the barrier agent does not affect the dissolution rate of the final product.

The hydromorphone, HPMC protected (optional) beads may then be overcoated with an aqueous dispersion of the hydrophobic polymer. The aqueous dispersion of hydrophobic polymer preferably further includes an effective amount of plasticizer, e.g. triethyl citrate. Pre-formulated aqueous dispersions of ethylcellulose, such as Aquacoat® or Surelease® may be used If Surelease® is used, it is not necessary to separately add a plasticizer.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic polymer. For example, color can be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable agents for providing color to the formulation when an aqueous dispersion of an acrylic polymer is used include titanium dioxide and color pigments, such as iron oxide pigments. The incorporation of pigments, may, however, increase the retardant effect of the coating.

The plasticized aqueous dispersion of hydrophobic polymer may be applied onto the substrate comprising the active agent by spraying using any suitable spray equipment known in the art. In a preferred method, a Wurster fluidized-bed system is used in which an air jet, injected from underneath, fluidizes the core material and effects drying while the hydrophobic polymer coating is sprayed on. A sufficient amount of the aqueous dispersion of hydrophobic polymer to obtain a predetermined controlled release of said active agent when said coated substrate is exposed to an environment of use, is preferably applied, taking into account considerations such as the physically characteristics of the active agent, the manner of incorporation of the plasticizer. After coating with the hydrophobic polymer, a further overcoat of a film-former, such as Opadry®, is optionally applied to the beads. This overcoat is provided, if at all, in order to substantially reduce agglomeration of the beads.

Next, the coated beads are cured in order to obtain a stabilized release rate of the active agent.

The optimum curing values for temperature, humidity and time for the particular formulation is determined experimentally. In certain embodiments of the present invention wherein the substrate is a pharmaceutically acceptable beads having the drug coated thereon, the beads which have been overcoated with the aqueous dispersion of plasticized ethylcellulose are stabilized via an oven curing conducted at a temperature of about 60° C. and a relative humidity from about 60% to about 100% for a time period from about 48 to about 72 hours. This is demonstrated with respect to the hydromorphone beads described in the examples provided below.

However, one skilled in the art will recognize that necessary curing conditions will be affected by the particular drug incorporated in the formulation, as well as by the thickness of the controlled release coating, the size of the substrate (e.g., beads as compared to tablets).

It is especially contemplated that the time period needed for curing to an endpoint as described above may actually be longer or shorter than the 48–72 hour time period mentioned above. Such curing times which achieve the intended result of a stabilized formulation are considered to be encompassed by the appended claims. Additionally, it will be appreciated by those skilled in the art that it may be possible to cure the aqueous dispersion coated substrates of the present invention in other manners in order to reach the endpoint at which the coated substrate provides a stable dissolution profile. Such additional curing methods which achieve the intended result of a stabilized formulation are also considered to be encompassed by the appended claims.

The curing endpoint may be determined by comparing the dissolution profile of the cured, coated substrate (e.g., the "formulation") immediately after curing (hereinafter referred to as "the initial dissolution profile") to the dissolution profile of the formulation after exposure to accelerated storage conditions. Generally, the curing endpoint may be determined by comparing the dissolution profile of the formulation after exposure to accelerated storage conditions of, e.g., 37° C./80% RH or 40° C./75% RH for a time period of one month to the initial dissolution profile. However, the curing endpoint may be further confirmed by continuing to expose the cured, coated formulation to accelerated storage conditions for a further period of time and comparing the dissolution profile of the formulation after further exposure of, e.g., two months and/or three months, to the initial dissolution profile obtained.

In certain preferred embodiments of the present invention in which the cured coated substrate is a pharmaceutical formulation, the curing endpoint is attained when the data points plotted along a graph of the dissolution curve obtained after, e.g., exposure to accelerated conditions of 1–3 months, show a release of the active agent which does not vary at any given time point by more than about 20% of the total amount of active agent released when compared to in-vitro dissolution conducted prior to storage. Such a difference in the in-vitro dissolution curves, referred to in the art as a "band range" or a "band width" of, e.g., 20%. In general, where the in-vitro dissolution prior to storage and after exposure to accelerated conditions varies by not more than, e.g., about 20% of the total amount of active agent released, the formulation is considered acceptable when considered by governmental regulatory agencies such as the U.S. FDA for stability concerns and expiration dating. Acceptable band ranges are determined by the FDA on a case-by-case basis, and any band range for a particular pharmaceutical which would be deemed acceptable by such a governmental regulatory agency would be considered to fall within the appended claims. In preferred embodiments, the aforementioned band range is not more than 15% of the total amount of active agent released. In more preferred embodiments, the band range is not more than 10% of the total amount of active agent released. In the appended Examples, the band range is often significantly less than 10%.

The release of the active agent from the controlled release formulation of the present invention can be further influenced, i.e., adjusted to a desired rate, by the addition of one or more release-modifying agents, or by providing one or more passageways through the coating.

The release-modifying agents which function as pore-formers can be inorganic or organic, and include materials that can be dissolved, extracted or leached from the coating in the environment of use.

For example, the pore-formers may comprise one or more water-soluble hydrophilic polymers in order to modify the release characteristics of the formulation. Examples of suitable hydrophilic polymers include hydroxypropylmethylcellulose, cellulose ethers, acrylic resins and protein-derived materials. Of these polymers, the cellulose ethers, especially hydroxyalkylcelluloses and carboxyalkylcelluloses, are preferred. Also, synthetic water-soluble polymers may be used, such as polyvinylpyrrolidone, cross-linked polyvinylpyrrolidone, polyethylene oxide, etc., and polysaccharides, e.g., pullulan, dextran, etc. In certain preferred embodiments of the present invention, the hydrophilic polymer comprises hydroxypropylmethylcellulose.

In addition, a water-soluble polydextrose that dissolves to a level of at least about 1% (W/W) in water at 25° C. may be incorporated into the controlled release coating.

The pore-formers further include alkali metal salts, polysaccharides, such as lithium carbonate, sodium chloride, sodium bromide, potassium chloride, potassium sulfate, potassium phosphate, sodium acetate, sodium citrate, and the like. Suitable polysaccharides include sucrose, glucose, fructose, mannitol, lactose, mannose, galactose, sorbitol and the like. The pore-forming solids may also be polymers which are soluble in the environment of use, such as Carbowaxes®, Carbopol®, and the like. The pore-formers embrace diols, polyols, polyhydric alcohols, polyalkylene glycols, polyglycols, poly(a-w)alkylenediols, and the like. The pore-formers are non-toxic and on their removal from lamina, channels and pores are formed through the lamina that fill with fluid present in the environment use.

Semipermeable polymers may also be incorporated in the controlled release coating to change the release characteristics of the formulation. Such semipermeable polymers include, for example, cellulose acylate, cellulose diacylate, cellulose triacylate, cellulose acetate, cellulose diacetate, cellulose triacetate, betaglucan acetate, acetaldehyde dimethyl acetate, cellulose acetate ethyl carbamate, polyamide, polyurethane, sulfonated polystyrene, cellulose acetate phthalate, cellulose acetate methyl carbamate, cellulose acetate succinate, cellulose acetate dimethylaminoacetate, cellulose acetate chloracetate, cellulose dipalmitate, cellulose dioctanoate, cellulose dicaprylate, cellulose dipentanlate, cellulose acetate valerate, cellulose acetate p-toluenesulfonate, cellulose acetate butyrate, and other semipermeable polymers such as those described in U.S. Pat. No. 4,285,987 (hereby incorporated by reference), as well as the selectively permeable polymers formed by the coprecipitation of a polycation and a polyanion as disclosed in U.S. Pat. Nos. 3,173,876; 3,276,586; 3,541,005; 3,541,006 and 3,546,142 (hereby incorporated by reference).

The controlled release coatings of the present invention can also include other release-modifying agents such as cellulose acetate phthalate, such as those disclosed in U.S. Pat. No. 2,196,768, herein incorporated by reference. Other suitable release-controlling agents which may be included in the controlled release coating of the present invention include shellac, zein, hydroxypropylmethyl cellulose phthalate, sandarac, modified shellac, etc.

The controlled release coatings of the present invention can also include released modifying agents which promote erosion (i.e., erosion promoting agents), such as starch (including, but not limited to corn starch, rice starch, α starch, carboxymethyl starch, potato starch, and other vegetable starches), modified starch, and starch derivatives. This category is also intended to include other erosion-promoting agents such as gums, including but not limited to xanthan gum, alginic acid, other alginates, bentonite, vee-gum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, etc.

The controlled release coatings of the present invention can also include release-modifying agents which are useful for making microporous lamina in the environment of use, such as polycarbonates comprised of linear polyesters of carbonic acid in which carbonate groups reoccur in the polymer chain, microporous materials prepared by the phosgenation of a dihydroxyl aromatic such as bisphenol, a microporous poly(vinylchloride), microporous polyamides such as polyhexamethylene adipamide, microporous modacrylic copolymers including those formed from poly-(vinychloride) and acrylonitrile, microporous styrene-acrylic and its copolymers, porous polysulfones having a diphenylene sulfone in a linear chain thereof, halogenated poly(vinylidene), polychloroethers, acetal polymers, polyesters prepared by esterification of a dicarboxylic acid or anhydride with an alkylene polyol, poly(alkylenesulfides), phenolics, polyesters, microporous polysaccharides having substituted an hydroglucose units exhibiting a decreased permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,601; 3,852,224; 3,852,388; and 3,853,601 (all of which are hereby incorporated by reference); in British Pat. No. 1,126,849; and in Chem. Abst. Vol. 71, 427F, 22573F, 1969.

Additional microporous materials for forming microporous lamina include poly(urethane), cross-linked chain-extended poly(urethane), poly(imides), poly(benzimidazoles), collodion, regenerated proteins, semi-solid cross-linked poly(vinylpyrrolidone), microporous materials prepared by diffusion of multivalent cations into polyelectrolyte sols, microporous derivatives of poly(styrene) such as poly-(sodium-styrenesulfonate), poly(vinyl benzyl trimethyl-ammonium chloride), microporous cellulosic acrylates and the like microporous polymers such as those described in U.S. Pat. Nos. 3,524,753; 3,565,259; 3,276,589; 3,541,055; 3,541,006; 3,546,142; 3,615,024; 3,646,178, and 3,852,224 (all of which are hereby incorporated by reference).

In certain preferred embodiments of the present invention, the release-modifying agent is hydroxypropylmethylcellulose, lactose, metal stearates, or mixtures thereof.

In general, the amount of release-modifying agent included in the controlled release coatings of the present invention may be from about 0.1% to about 80%, by weight, relative to the combined weight of hydrophobic polymer (e.g., ethylcellulose) and release-modifying agent. In general, the ratio of hydrophobic polymer to hydrophilic polymer is from about 99:1 to about 20:80, by weight. In certain preferred embodiments, the controlled release formulations of the present invention include from about 0.1% to about 50%, and in most preferred embodiments from about 0.1% to about 25%, by weight, relative to the combined weight of the hydrophobic polymer and release-modifying agent.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

The active agent(s) included in the controlled release formulations of the present invention include systemically active therapeutic agents, locally active therapeutic agents, disinfecting agents, chemical impregnants, cleansing agents, deodorants, fragrances, dyes, animal repellents, insect repellents, a fertilizing agents, pesticides, herbicides, fungicides, and plant growth stimulants, and the like.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, antispasmodics (e.g. atropine, scopolamine), antidiabetics (e.g., insulin), diuretics (e.g., ethacrynic acid, bendrofluazide), antihypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

In certain preferred embodiments, the therapeutically active agent comprises hydromorphone, oxycodone, dihydrocodeine, codeine, dihydromorphine, morphine, buprenorphine, salts of any of the foregoing, mixtures of any of the foregoing, and the like.

In another preferred embodiment of the present invention, the active agent is a locally active therapeutic agent and the environment of use may be, e.g., the gastrointestinal tract, or body cavities such as the oral cavity, periodontal pockets, surgical wounds, the rectum or vagina.

The locally active pharmaceutical agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive.

When the controlled release coating of the present invention is to be applied to tablets, the tablet core (e.g. the substrate) may comprise the active agent along with any pharmaceutically accepted inert pharmaceutical filler (diluent) material, including but not limited to sucrose, dextrose, lactose, microcrystalline cellulose, xylitol, fructose, sorbitol, mixtures thereof and the like. Also, an effective amount of any generally accepted pharmaceutical lubricant, including the calcium or magnesium soaps may be added to the above-mentioned agents of the excipient prior to compression of the tablet core agents. Most preferred is magnesium stearate in an amount of about 0.2–3% by weight of the solid dosage form.

In another preferred embodiment of the present invention, the active agent is disinfecting agent, e.g. a chlorine compound such as calcium hypochlorite, and the environment of use is a surrounding body of water, e.g. a recreational pool.

In still another preferred embodiment of the present invention, the active agent comprises at least one of a cleansing agent, a germicide, a deodorant, a surfactant, a fragrance, a perfume, a sanitizer, and/or a dye, and the environment of use is an aqueous solution, e.g. a urinal or toilet bowl.

In yet another preferred embodiment of the present invention, the active agent is a chemical impregnant, e.g. fertilizer, animal repellents, insect repellents, pesticides, herbicides, fungicides, plant growth stimulants, and the environment of use is, e.g., anywhere around the home, e.g. soil, trees etc. The fertilizer may be, for example, a nitrogen containing compound such as urea, urea formaldehyde composites, potassium nitrate, potassium sulfate, potassium chloride, ammonium nitrate, ammonium sulfate, monoammonium phosphate, dibasic ammonium phosphate, ammoniated super-phosphoric acid, micronutrient ingredients such as trace elements of iron, zinc, manganese, copper, boron, molybdenum, and mixtures of any of the foregoing. The fertilizer may be, e.g., in granular form.

For example, when the coated substrate is a coated chlorine tablet for combatting bacterial and algaecidal contamination of swimming pools and the like, the substrate may comprise commercial grade calcium hypochlorite, with or without trichloroisocyanuric acid, sodium dichlorocyanurate, lithium hypochlorite, powdered lime, and/or the like.

For example, the substrate may comprise about 98.5% commercial grade calcium hypochlorite and about 1.5% powdered lime, by weight. The substrate may also comprise commercial granular calcium hypochlorite, up to 20% by weight chloride of lime, and 1% zinc stearate having an available chlorine percentage of about 69% and a mass of about 57 g and a diameter of about 40 mm, as described in U.S. Pat. No. 4,192,763, hereby incorporated by reference. The substrate is then coated with the aqueous dispersion of plasticized hydrophobic polymer to a weight gain from about 3 to about 30 percent, depending upon the desired rate of dissolution, and the coated tablet is then cured in accordance with the present invention until an endpoint is reached at which the cured coated tablet provides a reproducibly stable dissolution profile.

When the active agent comprises a composition suitable for cleaning and preventing the staining of toilet bowls, the substrate may include a well-known disinfectant such as calcium hypochlorite and/or trichloroisocyanuric acid. The active agent may alternatively comprise an alkali metal salt of dichloroisocyanuric acid and a chloride salt such as calcium chloride and barium chloride, such as that which is described in U.S. Pat. No. 4,654,341, hereby incorporated by reference.

One possible example of such a product might include a substrate comprising 0.5–5% fragrance, 1–10% dye, 10–40% surfactant (which may be nonionic, cationic, anionic or zwitterion surfactants), and other optional components such as germicides, disinfectants, processing aids, and other commonly included ingredients known to those skilled in the art. Such active agents may be incorporated into a substrate comprising a tablet, along with other well-known ingredients such as detergents, surfactants, perfumes, dyes, and any necessary fillers.

The substrate may be alternatively comprise a pellet which is prepared by homogenously mixing together, e.g., 1 g of azure blue dye 65% (dye commercially available from Hilton David), 1 g Pluronic F-127 (a nonionic surfactant comprising the condensation products of ethylene oxide with the product resulting from the reaction of propylene oxide and ethylene diamine; commercially available from BASF-Wyandote Chemicals), 38 g Carbowax 8000 (a solid polyethylene glycol, molecular weight 8000; commercially available from Union Carbide), and 40 g Kemamide U (a oleylamide surfactant; commercially available from Witco) and an optional fragrance (e.g., 0.5% by weight citrus pine fragrance), and thereafter processing the above ingredients into a pellet by conventional methods such as noodling, plodding, extruding and cutting and stamping the mass to form the pellets. Optionally, the pellets may also include a suitable amount of an inorganic salt to cause the pellet to settle to the tank bottom, and one or binding agents such as guar gum. The pellet is then coated with the aqueous dispersion of plasticized hydrophobic polymer to a weight gain from about 2 to about 30 percent, depending upon the desired rate of dissolution, and the coated pellet is then cured in accordance with the present invention until an endpoint is reached at which the cured coated pellet provides a reproducibly stable dissolution profile.

Another example of a substrate useful for the treatment of the flush water of toilets is one which comprises an iodophor such as povidone iodine, as described in U.S. Pat. No. 5,043,090, hereby incorporated by reference.

When the substrate comprises a fragrance, the fragrance may be any conventional commercially available perfume oil, e.g., volatile compounds including esters, ethers aldehydes, alcohols, unsaturated hydrocarbons, terpenes, and other ingredients which are well known in the art. Their type and compatibility is limited only by their compatibility and desirability, as may be determinable by those skilled in the art.

When the active agent comprises a composition suitable for use as a fertilizer, the active agent may comprise granular urea which is coated with the aqueous dispersion of plasticized hydrophobic polymer to a weight gain from about 2 to about 30 percent and then cured in accordance with the present invention. In urea pill production, urea at 70% solids concentration in water is heated to remove substantially all of the water. The molten urea is then injected as droplets to an air cooling tower where crystalline urea is formed as a hard pill or bead, which is then coated and cured in accordance with the present invention.

When the substrate comprises plant food formulations, the substrate can be pelleted, ball-shaped, particulate, or in stick form, and may additionally contain growth promoting substances such as gibberellic acid along with soil fungistats such as formaldehyde and paraformaldehyde, etc.

In certain embodiments of the present invention, the coated substrate includes an additional dose of active agent included in either the controlled release coating comprising the aqueous dispersion of hydrophobic polymer, or in an additional overcoating coated on the outer surface of the controlled release coating. This may be desired when, for example, a loading dose of a therapeutically active agent is needed to provide therapeutically effective blood levels of the active agent when the formulation is first exposed to gastric fluid.

Figure A is a Scanning Electron micrograph (SEM) of a theophylline bead coated in accordance with the present invention prior to curing, taken at a magnification of 18,000. The coating is an aqueous dispersion of ethylcellulose coated to a weight gain of 5%. The SEM shows the distinct particles of ethylcellulose on the coating. Due to cracks or pores in the coating, the coating allows the environmental fluid to pass through to the underlying core where the active agent is found.

Figure B is an SEM of the theophylline bead shown in Figure A, taken after the bead has been cured in an oven at 60° C. and at a relative humidity of about 85% for a time period of 72 hours. The SEM of Figure B is taken at a magnification of 15,000. The individual ethylcellulose particles have coalesced and fused to such an extent that further exposure to temperatures above the glass transition temperature of the aqueous dispersion and a relative humidity from about 60% to about 100% do not cause a further coalescence or fusion which would further change the dissolution profile of the coated substrate.

DETAILED DESCRIPTION OF THE PREFERRED EMBODIMENTS

The following examples illustrate various aspects of the present invention. They are not to be construed to limit the claims in any manner whatsoever. In the following tablets which report the results of dissolutions tests, the underlined numerals specify hours and the figures provided in the columns beneath these underlined numerals specify the percent active ingredient dissolved.

EXAMPLE 1

Hydromorphone beads were prepared by dissolving hydromorphone HCl in water, adding Opadry® Y-5-1442, light pink (a product commercially available from Coloron, West Point, Pa., which contains hydroxypropyl methylcellulose, hydroxypropyl cellulose, titanium dioxide, polyethylene glycol and D&C Red No. 30 Aluminum Lake), 20% w/w, and mixing for about 1 hour, and then spraying onto nu pariel 18/20 beads using a Wuster insert. The resultant coated beads were then overcoated with Opadry® Y-5-1442 light pink (15% w/w). The resultant preparation had the formula set forth in Table 1 below:

TABLE 1

| Ingredient | Percent | Amt/Unit |
|---|---|---|
| Hydromorphone HCl | 4.75% | 4 mg |
| Nu Pariel 18/20 | 87.9% | 74 mg |
| Opadry ® Lt. Pink Y-5-1442 | 2.4% | 2 mg |
| Opadry ® Lt. Pint Y-5-1442 (overcoat) | 5.0% | 4.2 mg |
| | 100.0% | 84.2 mg |

The hydromorphone, HPMC protected beads were then overcoated with 15% w/w Aquacoat® (including triethyl citrate), and then overcoated with Opadry® Light Pink 5% w/w after curing (see Table 2). The beads cured at high humidity were dried in a fluid bed before the final overcoat.

TABLE 2

| Composition After Coating | |
|---|---|
| Ingredient | Percent |
| Hydromorphone beads | 80.57% |
| Aquacoat ® ECD 30 | 12.06% |
| Triethyl citrate | 2.39% |
| Opadry ® Lt. Pink | 4.98% |
| Y-5-1442 (Overcoat) | |
| | 100% |

The product was then divided into four portions. In Example 1, the coated beads were placed in a 30 cc amber glass vial and cured in an oven for 72 hours at 60° C./85% relative humidity. In Comparative Example 1A, the coated beads were cured for 24 hours at 60° C. under dry conditions. In Comparative Example 1B, the coated beads were cured for 72 hours at 60° C. under dry conditions. In Comparative Example 1C, the coated beads were cured for 24 hours at 60° C. at 85% relative humidity.

All products cured at the four above-mentioned different conditions were then tested for stability under the following conditions: Room Temperature; 37° C. dry; 37° C./85% Relative Humidity (RH); 50° C. dry; 60° C. dry; and 60° C./85% RH.

The relative humidity in a water-filled desiccator in a 60° C. oven was determined as follows. First, about 500 grams of purified water is poured into a plastic desiccator and the metal guard inserted. A hygrometer/temperature indicator is placed on top of the guard and the desiccator covered and placed in the 60° C. oven for 24 hours. After 24 hours the relative humidity in the desiccator was 85% while the temperature was still 60° C. On placing the hygrometer alone in the 60° C. oven for 24 hours, the relative humidity was 9% at 60° C.

The dissolution tests were carried out via the USP Basket Method, 37° C., 100 RPM, first hour 700 ml gastric fluid at pH 1.2, then changed to 900 ml at pH 7.5. In each instance, the dissolution was conducted by placing an open capsule containing the specified amount of cured beads (8 mg hydromorphone HCl, 209 mg beads ±10%) into a vessel.

It was observed that the dissolution of Example 1 did not change under these accelerated conditions, except that changes were seen with respect to the extreme conditions of 60° C./85% RH. The results for Example 1 are set forth in Tables 3–8 below:

TABLE 3

| | ROOM TEMPERATURE | | | | | | | |
|---|---|---|---|---|---|---|---|---|
| | Hydro-morphone HCl | Dissolution | | | | | | |
| Time (wks) | (Amount) | 1 | 2 | 4 | 8 | 12 | 18 | 24 |
| Initial | 8.14 mg | 0 | 4.6 | 29.5 | 52.6 | 64.7 | 76.6 | 82.8 |
| 1 | 7.95 mg | 0 | 5.1 | 30.3 | 55.0 | 67.4 | 79.8 | 88.9 |
| 4 | 7.80 mg | 1.3 | 8.2 | 33.5 | 57.4 | 70.0 | 82.8 | 90.9 |
| 8 | 7.78 mg | 0.7 | 6.0 | 30.5 | 54.0 | 66.4 | 78.0 | 88.2 |

TABLE 4

37° C. DRY

| Time (wks) | Hydro-morphone HCl (Amount) | Dissolution | | | | | | |
|---|---|---|---|---|---|---|---|---|
| | | 1 | 2 | 4 | 8 | 12 | 18 | 24 |
| Initial | 8.14 mg | 0 | 4.6 | 29.5 | 52.6 | 64.7 | 76.6 | 82.8 |
| 1 | 7.96 mg | 0 | 6.0 | 30.8 | 55.3 | 68.0 | 81.6 | 89.7 |
| 4 | 7.91 mg | 2 | 8.1 | 33.2 | 56.6 | 70.2 | 82.0 | 91.3 |
| 8 | 7.73 mg | 1 | 5.8 | 31.3 | 57.5 | 64.6 | 82.7 | 91.6 |

TABLE 5

37° C./80% RH

| Time (wks) | Hydro-morphone HCl (Amount) | Dissolution | | | | | | |
|---|---|---|---|---|---|---|---|---|
| | | 1 | 2 | 4 | 8 | 12 | 18 | 24 |
| Initial | 8.19 mg | 0 | 4.6 | 29.5 | 52.6 | 64.7 | 76.6 | 82.8 |
| 1 | 7.85 mg | 0 | 5.6 | 31.0 | 55.1 | 68.5 | 80.3 | 89.1 |
| 4 | 8.16 mg | 2.4 | 7.6 | 32.3 | 52.8 | 64.4 | 75.4 | 82.7 |
| 8 | 8.22 mg | 2.9 | 7.9 | 33.5 | 53.3 | 64.5 | 73.6 | 81.3 |

TABLE 6

50° C. (dry)

| Time (wks) | Hydro-morphone HCl (Amount) | Dissolution | | | | | | |
|---|---|---|---|---|---|---|---|---|
| | | 1 | 2 | 4 | 8 | 12 | 18 | 24 |
| Initial | 8.14 mg | 0 | 4.6 | 29.5 | 52.6 | 64.7 | 76.6 | 82.8 |
| 1 | 8.14 mg | 0 | 6.3 | 32.7 | 56.3 | 68.3 | 80.8 | 89 |
| 4 | 7.81 mg | 2.3 | 10 | 37.0 | 59.6 | 72.0 | 84.5 | 92 |
| 8 | 7.74 mg | 2 | 10.4 | 35.8 | 59.2 | 71.3 | 82.3 | 90.5 |

TABLE 7

60° C. (dry)

| Time (wks) | Hydro-morphone HCl (Amount) | Dissolution | | | | | | |
|---|---|---|---|---|---|---|---|---|
| | | 1 | 2 | 4 | 8 | 12 | 18 | 24 |
| Initial | 8.14 mg | 0 | 4.6 | 29.5 | 52.6 | 64.7 | 76.6 | 82.8 |
| 1 | 8.13 mg | 0 | 6.7 | 34.6 | 57.8 | 70.3 | 82.1 | 90.5 |
| 4 | 8.30 mg | 2.7 | 10.6 | 36.6 | 56.8 | 68.7 | 80.4 | 85.6 |
| 8 | 7.94 mg | 3.6 | 11.9 | 37.4 | 58.4 | 71.1 | 80.6 | 89.3 |

TABLE 8

60° C./100% RH

| Time (wks) | Hydro-morphone HCl (Amount) | Dissolution | | | | | | |
|---|---|---|---|---|---|---|---|---|
| | | 1 | 2 | 4 | 8 | 12 | 18 | 24 |
| Initial | 8.14 mg | 0 | 4.6 | 29.5 | 52.6 | 64.7 | 76.6 | 82.8 |
| 1 | 7.26 mg | 6.1 | 9.9 | 23.4 | 42.4 | 53.3 | 63.1 | 72.5 |
| 4 | 6.64 mg | 19 | 23.7 | 32.5 | 41.4 | 46.7 | 53.0 | 51.7 |
| 8 | 5.38 mg | 25.1 | 28.4 | 33.2 | 40.0 | 44.1 | 47.7 | 52.0 |

The data provided in Table 5 shows that despite exposure to accelerated conditions, the change in amount of hydromorphone released at each time point was insignificant. The largest band range occurred at 24 hours (after 2 month storage), where the difference in amount released is 1.5%.

In contrast, the dissolution profiles of Comparative Examples 1A, 1B and 1C continued to slow down (e.g., cure) at all accelerated conditions. The results are set forth in Tables 9, 10 and 11, respectively. The widest point of the band range for Comparative Example 1A was 22.4% (at 4 hours dissolution). The widest point of the band range for Comparative Example 1B is 17.3% (at 12 hours dissolution). The widest point of the band range for Comparative Example 1C is, in contrast, only 9.1% (at 18 hours dissolution). The fact that the results of Comparative Example 1C represent substantial improvement as compared to the results of Comparative Examples 1A and 1B is not surprising, as this was the only comparative example which utilized curing at high relative humidity conditions.

TABLE 9

Comparative Example 1A

| Conditions/ Time | Hydromorphone HCl (Amount) | Dissolution | | | | | | |
|---|---|---|---|---|---|---|---|---|
| | | 1 | 2 | 4 | 8 | 12 | 18 | 24 |
| Initial | 9.03 mg | 17.8 | 43.6 | 63.6 | 78.8 | 86.7 | 94.7 | 94.2 |
| Room Temp. 8 wks | 8.79 mg | 18.4 | 35.9 | 58.2 | 76.3 | 88.7 | 97 | * |

TABLE 9-continued

Comparative Example 1A

| Conditions/ Time | Hydromorphone HCl (Amount) | Dissolution | | | | | | |
|---|---|---|---|---|---|---|---|---|
| | | 1 | 2 | 4 | 8 | 12 | 18 | 24 |
| 37° C. (dry) 8 wks | 8.50 mg | 14 | 36.5 | 59.1 | 81.1 | 91.4 | 99.4 | * |
| 37° C./80% RH 8 wks | 8.15 mg | 6.6 | 23.6 | 41.2 | 60.7 | 72.3 | 83.1 | * |
| 50° C. (dry) 8 wks | 8.45 mg | 17.3 | 36 | 56.1 | 78.1 | 89.1 | 97.1 | 102.6 |
| 60° C. (dry) 8 wks | 8.65 mg | 7.3 | 28.5 | 48.9 | 64.4 | 82 | 92.3 | 99.1 |
| 60° C./100% RH 8 wks | 5.81 mg | 17.5 | 22.6 | 28.8 | 36.5 | 41.7 | 46.5 | 50.3 |

TABLE 10

Comparative Example 1B

| Conditions/ Time | Hydromorphone HCl (Amount) | Dissolution | | | | | | |
|---|---|---|---|---|---|---|---|---|
| | | 1 | 2 | 4 | 8 | 12 | 18 | 24 |
| Initial | 8.82 mg | 4.7 | 35.5 | 58.3 | 75.6 | 87.3 | 96.0 | 98.2 |
| Room Temp. 8 wks | 8.29 mg | 8.7 | 34.6 | 59.3 | 80.8 | 92.1 | 99.2 | 105.7 |
| 37° C. (dry) 8 wks | 8.34 mg | 8.3 | 36.1 | 55.9 | 77.4 | 87.3 | 97.8 | 103.1 |
| 37° C./80% RH 8 wks | 8.86 mg | 4.9 | 25.4 | 43.6 | 61.7 | 70 | 80 | 87.2 |
| 50° C. (dry) 8 wks | 8.71 mg | 10.8 | 35.4 | 55.9 | 77.2 | 88.9 | 99.5 | 103.2 |
| 60° C. (dry) 8 wks | 8.30 mg | 5.3 | 32 | 54.1 | 76.6 | 87.2 | 99.8 | 105.5 |
| 60° C./100% RH 8 wks | 6.22 mg | 16.3 | 21.2 | 27.4 | 35.9 | 40.5 | 46.2 | 49.4 |

TABLE 11

Comparative Example 1C

| Conditions/ Time | Hydromorphone HCl (Amount) | Dissolution | | | | | | |
|---|---|---|---|---|---|---|---|---|
| | | 1 | 2 | 4 | 8 | 12 | 18 | 24 |
| Initial | 8.71 mg | 0.7 | 15.3 | 41.9 | 60.7 | 71.2 | 82.4 | 86.7 |
| Room Temp. 8 wks | 8.40 mg | 1 | 14.2 | 39.8 | 58.8 | 69.1 | 79.1 | 87.2 |
| 37° C. (dry) 8 wks | 8.84 mg | 2.7 | 14.5 | 40.5 | 60.4 | 71 | 81.3 | 89.8 |
| 37° C./80% RH 8 wks | 8.78 mg | 2.5 | 12.4 | 37.8 | 54.6 | 63.8 | 73.3 | * |
| 50° C. (dry) 8 wks | 8.71 mg | 3.2 | 17.5 | 42.3 | 61.1 | 70.8 | 81 | 87.9 |
| 60° C. (dry) 8 wks | 8.57 mg | 2.9 | 18.2 | 43.4 | 62.5 | 73.6 | 84.3 | * |
| 60° C./100% RH 8 wks | 6.10 mg | 15.7 | 20.3 | 26.4 | 33.8 | 38.3 | 43.1 | 46.7 |

FIG. 1 is a graphical representation of the dissolution results obtained with Example 1, comparing the initial dissolution profile with the dissolution profile after 8 weeks storage at 37° C./80%RH.

Figure 2:
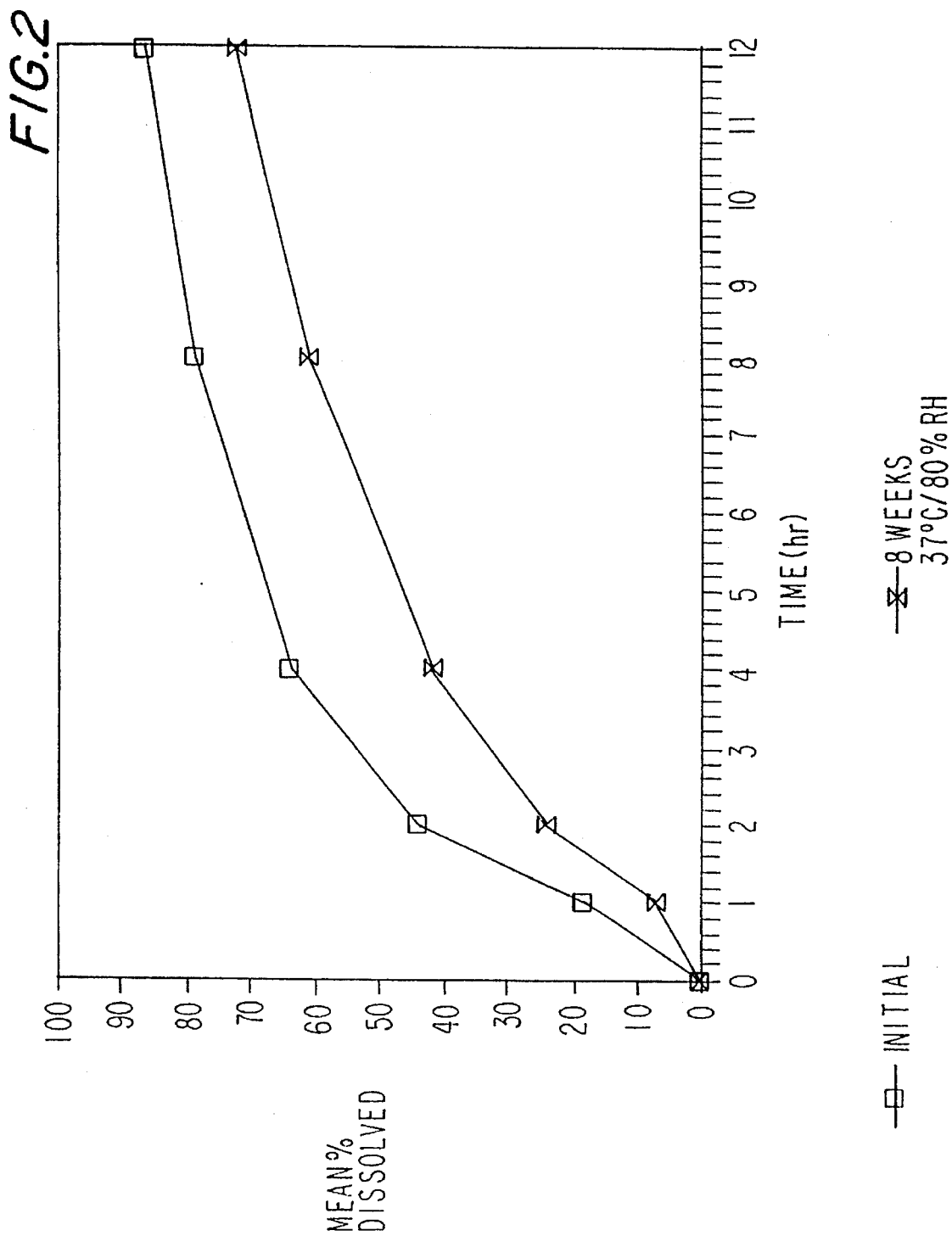
FIG. 2 is a graphical representation of the dissolution stability results of Comparative Example 1A.

FIG. 2 is a graphical representation of the dissolution profile of Comparative Example 1A, comparing the initial dissolution profile with the dissolution profile after 8 weeks storage at 37° C./80%RH.

Figure 3:
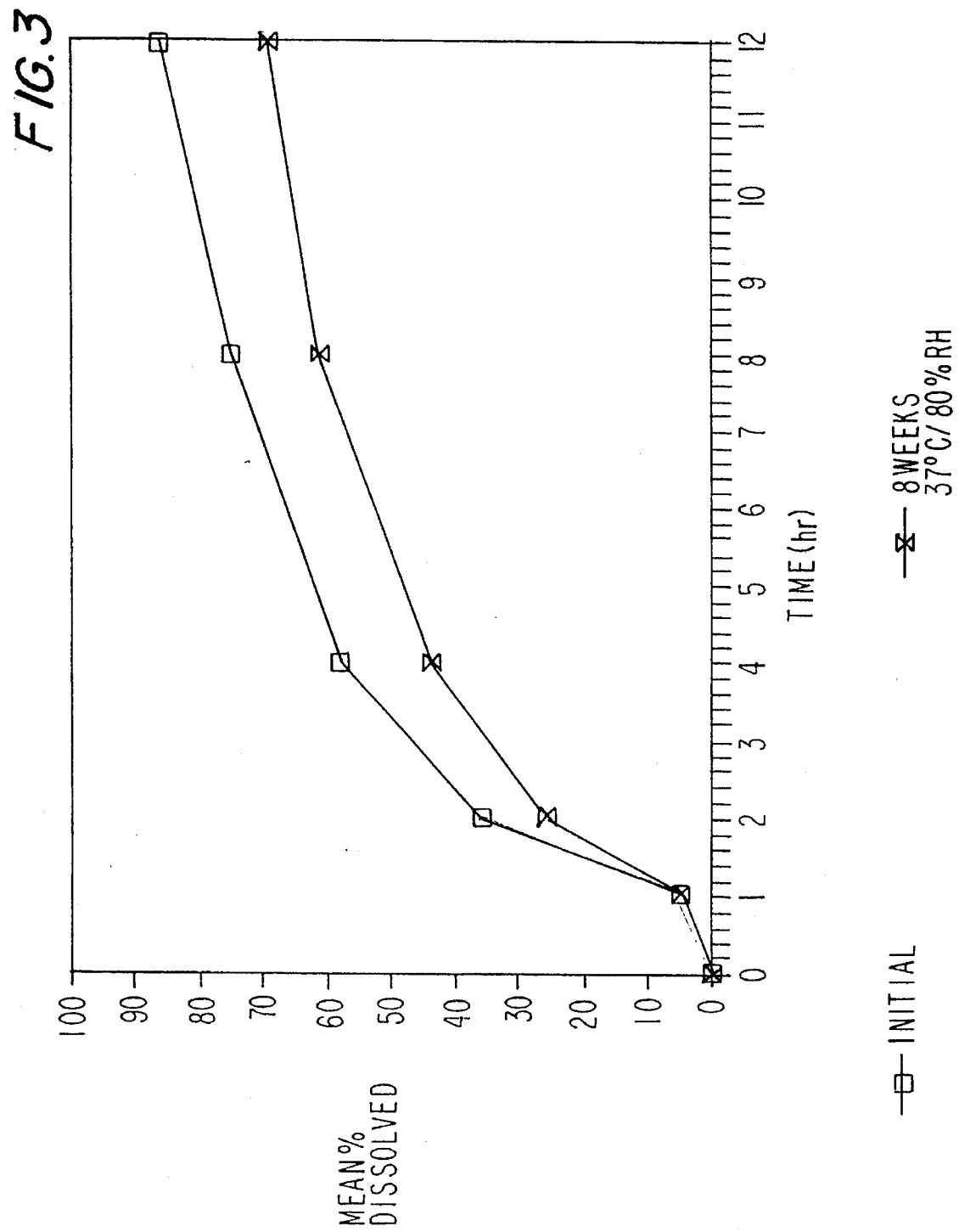
FIG. 3 is a graphical representation of the dissolution stability results of Comparative Example 1B.

FIG. 3 is a graphical representation of the dissolution profile of Comparative Example 1B, comparing the initial dissolution profile with the dissolution profile after 8 weeks storage at 37° C./80%RH.

Figure 4:
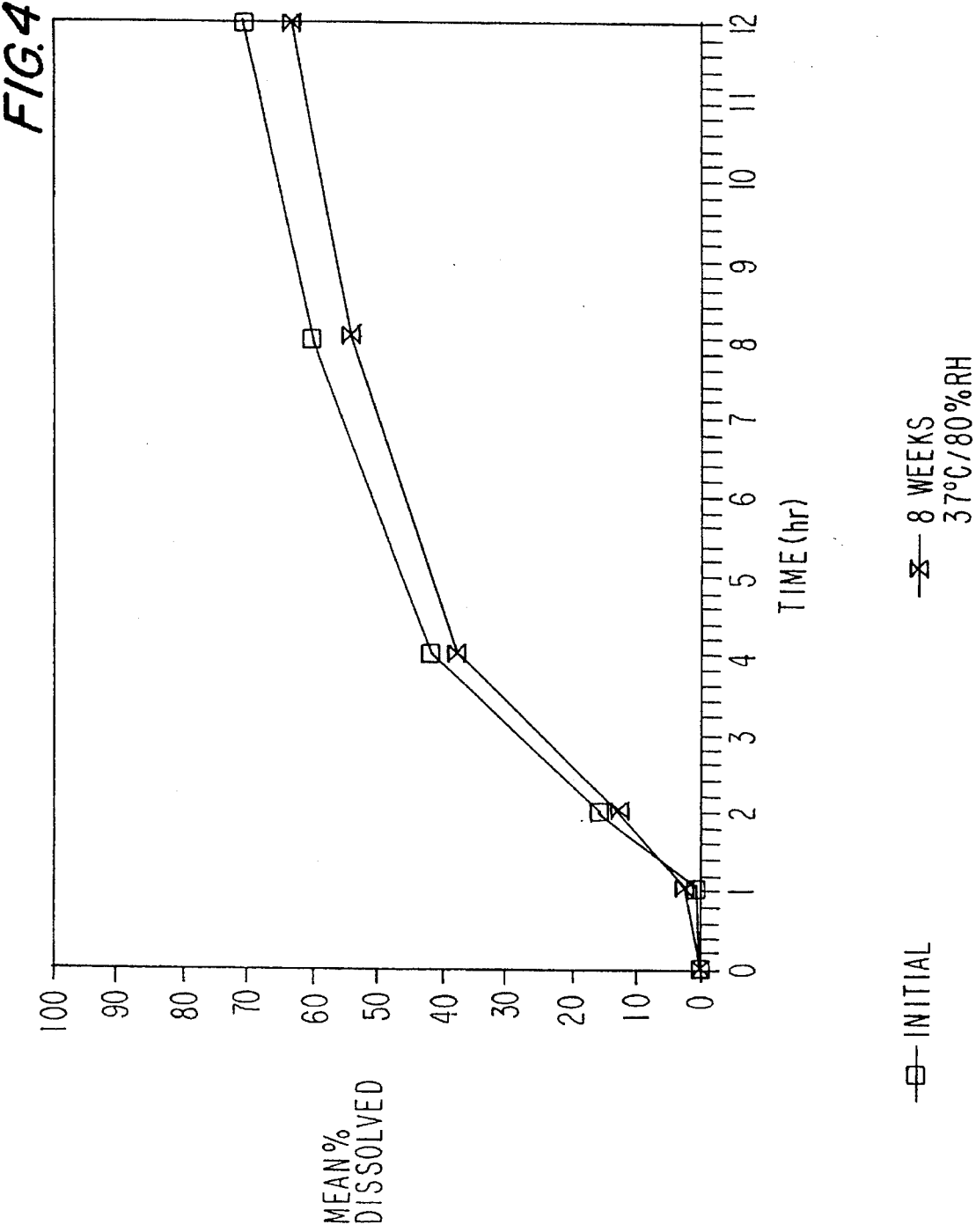
FIG. 4 is a graphical representation of the dissolution stability results of Comparative Example 1C.

FIG. 4 is a graphical representation of the dissolution profile of Comparative Example 1C, comparing the initial dissolution profile with the dissolution profile after 8 weeks storage at 37° C./80%RH-Comparing the results depicted in FIG. 1 (Example 1) with the results depicted in FIGS. 2–4 (the comparative examples), it is readily apparent that only in Example 1 were the initial and 8 week dissolution profiles substantially identical under storage conditions of 37° C./80%RH.

Figure 5:
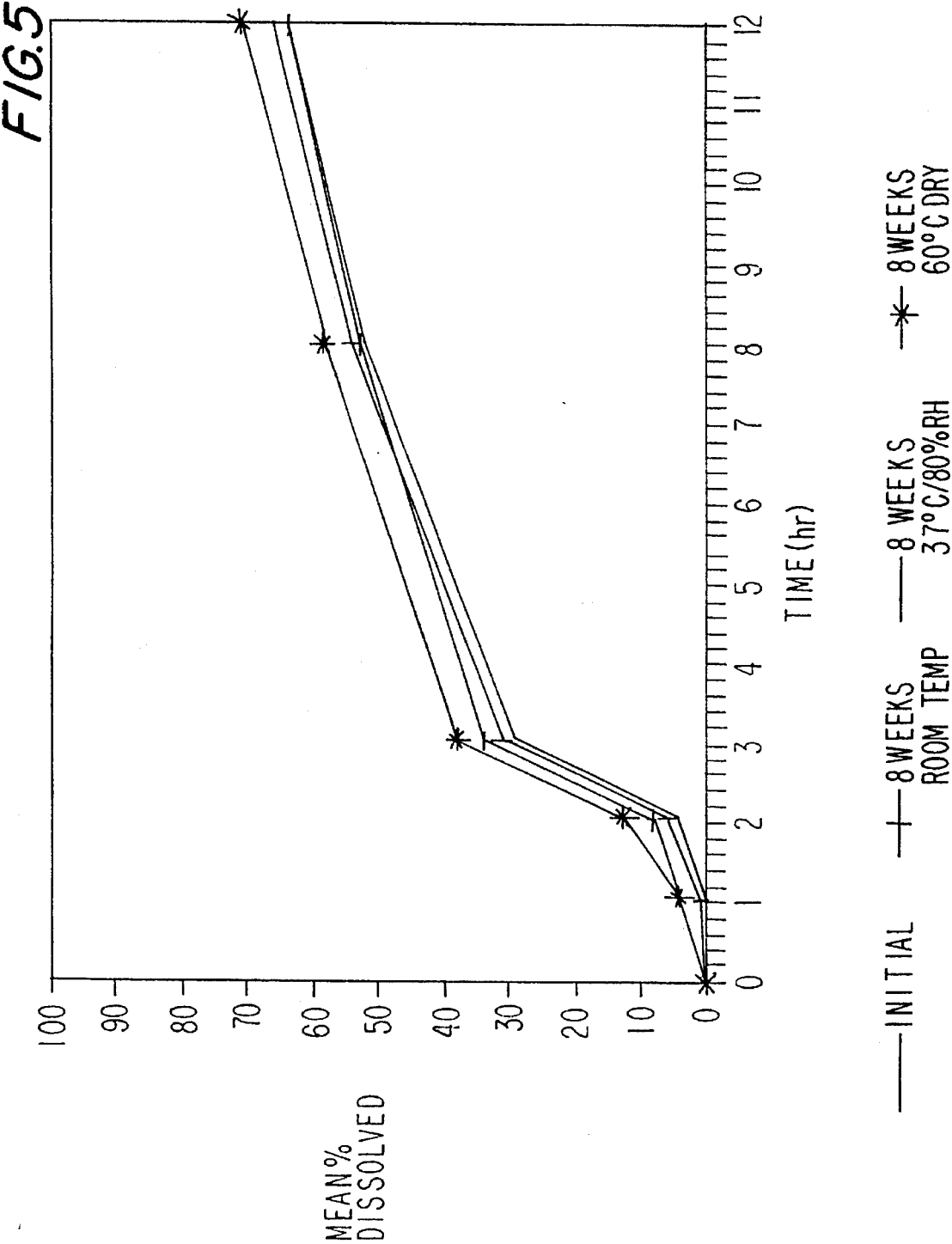
FIG. 5 is a graphical representation of the dissolution stability results of Example 1, comparing the dissolution profiles obtained under various conditions.

FIG. 5 is a graphical representation of the dissolution profiles of Example 1, comparing the initial dissolution profile with the dissolution profiles obtained after 8 weeks storage under various conditions (room temperature; 37° C./80%RH; and 60° C. dry). The dissolution profiles of Example 1 after 8 weeks under these various conditions is seen to be substantially identical.

Figure 6:
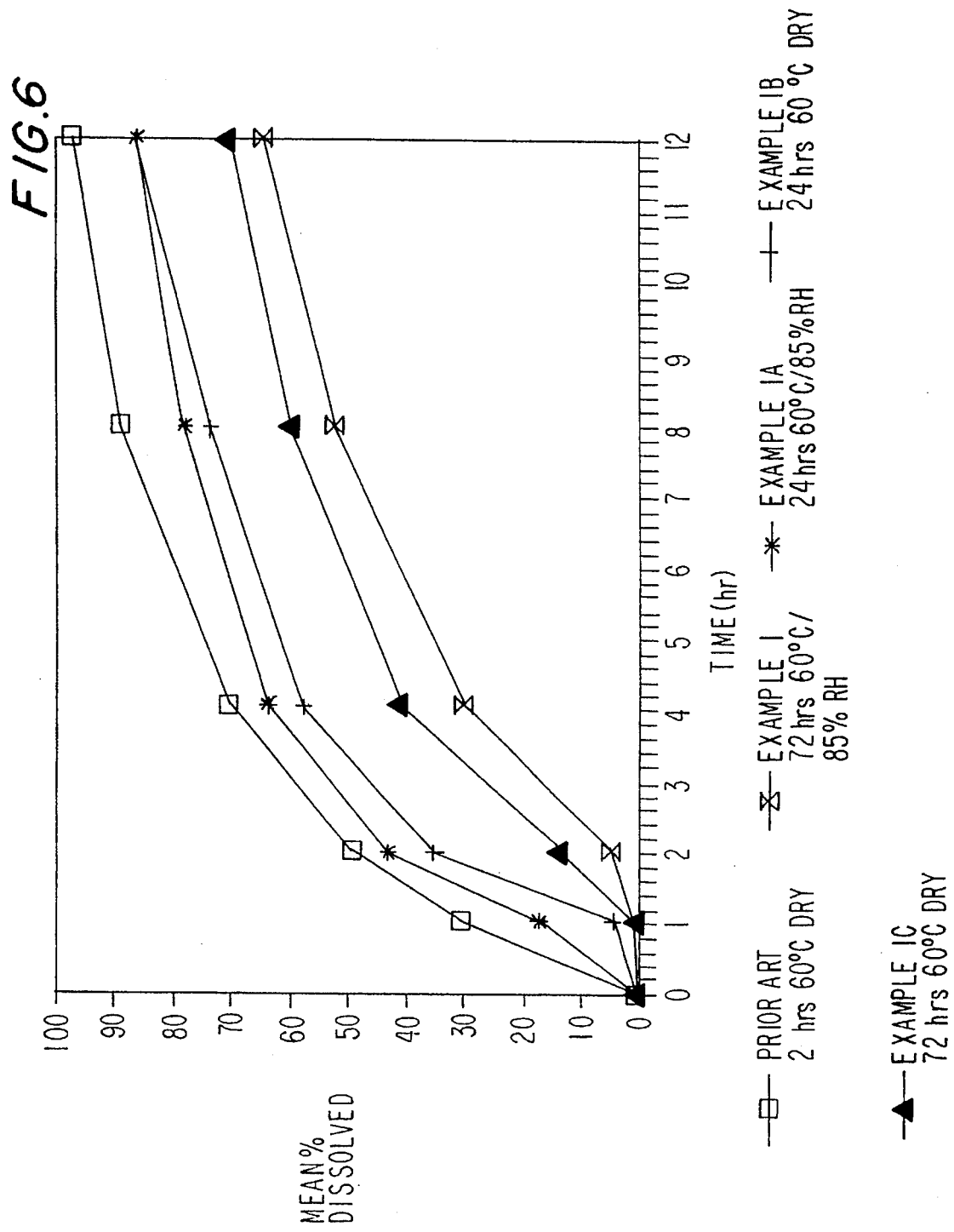
FIG. 6 is a graphical representation of the initial dissolution profiles obtained under various curing conditions.

Finally, FIG. 6 is a graphical representation of the initial dissolution profiles obtained after various curing conditions (curing of 2 hrs at 60° C. dry (the prior art); 72 hrs at 60° C./85%RH (Example 1); 24 hrs at 60° C. dry (Comparative Example 1A); 72 hrs at 60° C. dry (Comparative Example 1B); and at 60° C. at 85% RH for 24 hours (Comparative Example 1C)).

EXAMPLE 2—Curing at 60° C. Dry Heat—Longer Drying

In Example 2, hydromorphone HCl beads were prepared in accordance with Example 1 in order to determine if the stabilized initial dissolution achieved after curing at 60° C./85%RH could instead be achieved by a longer drying period without humidity. After coating with Aquacoat®, a further overcoat of Opadry® Y-5-1442, light pink is applied to the beads. The coated product had the composition set forth in Table 12 below:

TABLE 12

| Composition After Coating | | |
|---|---|---|
| Ingredient | Percent | Amt/Unit |
| Hydromorphone beads | 80.57% | 84.2 mg |
| Aquacoat ® ECD 30 | 12.06% | 12.6 mg |
| Triethyl citrate | 2.39% | 2.5 mg |
| Opadry ® Lt. Pink (Overcoat) | 4.98% | 5.2 mg |
| | 100.0% | 99.3 mg |

The Aquacoat® coated hydromorphone HCl beads were then cured in a 60° C. dry oven, and stored at 60° dry heat. The cured beads were placed in open gelatin capsules containing the specified amount of cured beads (about 8 mg hydromorphone HCl), and dissolution studies were then conducted in the manner set forth in Example 1 on three samples at the following time points: initial, 1 day, 2 days, 7 days, and 21 days in order to determine the stability of the dissolution profile. Dissolution studies were conducted as detailed above on the three samples. The mean results are set forth in Table 13 below:

TABLE 13

| Time (Days) | Wt (mg) | Dissolution (Time) | | | | | | |
|---|---|---|---|---|---|---|---|---|
| | | 1 hr | 2 hr | 4 hr | 8 hr | 12 hrs | 18 hrs | 24 hrs |
| Initial | 196.7 | 15.6 | 43.8 | 68.7 | 89.9 | 101.0 | 109.2 | 113.8 |
| 1 | 196.3 | 3.7 | 37.5 | 63.5 | 84.9 | 97.5 | 107.2 | 112.3 |
| 2 | 196.3 | 4.8 | 37.0 | 62.9 | 84.8 | 95.1 | 104.7 | 111.8 |
| 7 | 197.3 | 13.5 | 37.8 | 63.3 | 84.9 | 98.8 | 108.6 | 115.9 |
| 21 | 197.3 | 17.4 | 36.5 | 58.4 | 77.9 | 88.9 | 98.2 | 103.1 |

From the results set forth in Table 13 above, it is apparent that a profound slow down in release rate of the samples of Example 2 did not occur, as compared with the high temperature/high humidity condition of Example 1. This profound slow down is apparent when comparing, e.g. the initial dissolution of the drug in Tables 3–8 (Example 1) versus the initial dissolution of the drug in Table 13 (Example 2) (e.g., 0% vs. 15.6% release after one hour; 4.6% vs. 43.8% released after two hours; 29.5% vs. 68.7% released after four hours; etc.). The release rate for the drug in Example 2, however, would eventually slow down to a more similar rate to Example 1 after exposure to accelerated storage conditions. In other words, an endpoint was not reached at which the dissolution profile matches the base level of Example 1.

EXAMPLE 3—Increased Mixing Time

In Example 3, another attempt to stabilize Aquacoat® coated hydromorphone HCl beads using the premise that high temperature is not enough to insure complete coalescence of the ethylcellulose film. Normal time of mixing (and bonding) plasticizer and Aquacoat® is recommended by FMC to be 30 minutes. In Example 3, the contact time of the plasticizer (triethyl citrate) with the ethylcellulose polymer dispersion (Aquacoat®) was increased to 24 hours.

The coated beads were prepared in accordance with Example 1 and then placed in a 30 cc amber glass vial and cured in a 60° C. dry oven. Dissolution studies were then conducted on three samples at the following time points: 1 day, 2 days, 7 days and 11 days. Mean results are set forth in Table 14 below:

TABLE 14

| Time (Days) | Wt (mg) | Dissolution (Time) | | | | | | |
|---|---|---|---|---|---|---|---|---|
| | | 1 hr | 2 hr | 4 hr | 8 hr | 12 hr | 18 hrs | 24 hrs |
| 1 | 210.7 | 27.7 | 53.3 | 77.3 | 95.7 | 103.4 | 108.2 | 110.4 |
| 2 | 209.7 | 25.9 | 50.3 | 74.3 | 94.2 | 101.9 | 106.4 | 110.2 |
| 7 | 209.7 | 24.8 | 48.3 | 73.1 | 95.2 | 102.7 | 108.5 | 112.6 |
| 11 | 210.3 | 24.0 | 45.4 | 70.5 | 94.9 | 103.9 | 113.3 | 115.9 |

From the results set forth in Table 14 above, it is apparent that a profound slow down in release rate of the samples of Example 3 did not occur, as compared with the release rates both initially and under the high temperature/high humidity conditions of Example 1. In other words, an endpoint was not reached at which the dissolution profile gets down to the base level of Example 1. This profound slow down in release rate is apparent when comparing, e.g., the initial dissolution of the drug in Tables 3–8 (Example 1) versus the dissolution of the drug after one day storage (e.g., 0% vs. 27.7% release after one hour; 4.6% vs. 53.3% after two hours; 29.5% vs. 77.3% after four hours; etc.) .

EXAMPLE 4—Recommended Curing (Prior Art)

Hydromorphone beads were prepared by dissolving hydromorphone HCl in water, adding Opadry®, and mixing for about 1 hour, and then spraying onto nu pariel 18/20 beads using a Wurster insert. The resultant coated beads were then overcoated with Opadry® Y-5-1442 light pink (15% w/w). The beads were then overcoated with an aqueous dispersion of Aquacoat® to a 15% weight gain according to Table 15 below:

TABLE 15

| Ingredient | Percent (wt) | Amt/Unit |
| --- | --- | --- |
| Hydromorphone beads | 84.7 | 80 mg |
| Aquacoat ® CD 30 | 12.7 | 12 mg |
| Citroflex > 2A | 2.5 | 2.4 mg |
| (Triethylcitrate) | 99.9 | 94.4 mg |

After the resin was applied to the beads, the beads were cured in a fluid bed for about 2 hours at 60° C., as suggested in the literature and as recommended by FMC, since it is above the Tg for Aquacoat® plasticized with triethyl citrate at 20% level of solids.

The cured beads were then stored at room temperature, with dissolution studies being conducted initially and at 3 months. Samples were also stored at 37° C./80% RH. The mean results are provided in Table 16:

TABLE 16

| Time | Mean wt | 1hr | 2 hr | 4 hr | 8 hr | 12 hrs | 18 hrs | 24 hrs |
| --- | --- | --- | --- | --- | --- | --- | --- | --- |
| Initial | 283.2 | 30.4 | 44 | 70.2 | 89.1 | 97.0 | 101.3 | 102.1 |
| 3 mos | 282.3 | 36.2 | 57.8 | 76.9 | 89.0 | 93.4 | 96.6 | 98.5 |
| 37° C./80% RH | | | | | | | | |
| 1 mo | 288.4 | 0.5 | 26.7 | 50.5 | 69.6 | 80.7 | 90.7 | 97.0 |
| 2 mos | 287.3 | 0.6 | 25.1 | 50.7 | 70.3 | 81.6 | 92.2 | 98.8 |
| 3 mos | 293.7 | 1.2 | 23.7 | 48.6 | 65.6 | 74.5 | 80.2 | 83.5 |

From the results provided in Table 16 above, it can be seen that the dissolution profile of the samples stored at room temperature were acceptable. However, the dissolution of the samples slowed dramatically when stored at 37° C./80% RH. The band range for this example was unacceptably wide at, e.g., the one hour dissolution point (storage at 37° C./80% RH), as well as numerous other points.

Samples from the batch of Example 4 were repackaged, stored and thereafter subjected to heat under dry conditions at 37° C. and moisture (37° C./80% RH). The dissolution results are provided in Table 17 below:

TABLE 17

| Time | Mean wt | 1 hr | 2 hr | 4 hr | 8 hr | 12 hrs | 18 hrs | 24 hrs |
| --- | --- | --- | --- | --- | --- | --- | --- | --- |
| Initial | 283.2 | 30.4 | 49.0 | 70.3 | 89.1 | 97.0 | 101.3 | 102.1 |
| 37° Dry | | | | | | | | |
| 2 wks | 283.2 | 25.0 | 44.4 | 65.0 | 84.5 | 92.9 | 100.7 | 104.4 |
| 4 wks | 280.7 | 21.5 | 28.0 | 63.5 | 84.3 | 95.6 | — | — |
| 37° C./80% RH | | | | | | | | |
| 2 wks | 283.2 | 16.6 | 39.1 | 60.5 | 80.1 | 89.8 | 99.8 | 103.4 |
| 4 wks | 281.3 | 4.6 | 26.6 | 53.7 | 71.4 | 82.1 | — | — |

From the results set forth above, it is apparent that under dry conditions at 37° C., the dissolution of Example 4 did not come to the same endpoint as at 37° C./80% RH. Thus, the combination of both moisture and heat was required to complete the curing.

EXAMPLES 5–7

To test the effectiveness of high temperature (60° C.), high humidity curing as an effective process of stabilizing plasticized ethylcellulose controlled release films, Examples 5–7 were manufactured at different levels of Aquacoat® load.

In each of Examples 5–7, hydromorphone beads were made according to Example 1. Thereafter, overcoatings of 5% w/w, 10% w/w, and 15% w/w were applied to Examples 5–7 respectively, according to the formulas set forth in Tables 18–20:

TABLE 18

| Composition of Ex. 5 After Coating | | |
|---|---|---|
| Ingredient | Percent | Amt/Unit |
| Hydromorphone beads | 84.2% | 84.2 mg |
| Aquacoat® ECD 30 | 4.7% | 4.2 mg |
| Triethyl citrate | 0.9% | 0.84 mg |
| | 100% | 89.24 mg |

TABLE 19

| Composition of Ex. 6 After Coating | | |
|---|---|---|
| Ingredient | Percent | Amt/Unit |
| Hydromorphone beads | 89.3% | 84.2 mg |
| Aquacoat® ECD 30 | 8.9% | 8.4 mg |
| Triethyl citrate | 1.8% | 1.7 mg |
| | 100% | 94.3 mg |

TABLE 20

| Composition of Ex. 7 After Coating | | |
|---|---|---|
| Ingredient | Percent | Amt/Unit |
| Hydromorphone beads | 84.8% | 84.2 mg |
| Aquacoat® ECD 30 | 12.7% | 12.6 mg |
| Triethyl citrate | 0.9% | 2.5 mg |
| | 100% | 99.3 mg |

All three batches were cured in water loaded desiccators in a 60° C. oven. These batches were placed on screen trays in these desiccators after the Aquacoat® film was applied to the HPMC overcoated hydromorphone HCl bead. The desiccators containing the Aquacoat®-coated beads were then placed in a 60° C. oven for 72 hours. Thereafter, the batches were removed from the ovens. The beads appeared moist and therefore were dried in a lab line fluid bed dryer for one hour. They were then overcoated with 5% w/w Opadry® Y-5-1442 light pink in a wurster insert.

Stability studies on Examples 5–7 show the initial dissolutions to be the same as dissolutions done on samples placed at 37° C./80% RH conditions. The results are provided in Tables 21–23 below:

TABLE 21

| Dissolution (Time)-5% Aquacoat® | | | | | | | |
|---|---|---|---|---|---|---|---|
| Time (Days) | Wt (mg) | 1 hr | 2 hr | 4 hr | 8 hr | 12 hrs | 18 hrs | 24 hrs |
| Initial | 190 | 39.8 | 57.4 | 73.0 | 88.0 | 93.8 | 98.0 | 95.6 |
| 28 | 191 | 33.4 | 54.6 | 71.9 | 84.2 | 89.8 | 94.6 | 96.4 |

TABLE 22

| Dissolution (Time)-10% Aquacoat® | | | | | | | |
|---|---|---|---|---|---|---|---|
| Time (Days) | Wt (mg) | 1 hr | 2 hr | 4 hr | 8 hr | 12 hrs | 18 hrs | 24 hrs |
| Initial | 200.3 | 7.5 | 27.9 | 48.5 | 68.1 | 76.2 | 90.3 | 88.9 |
| 28 | 210 | 9.9 | 32.4 | 52.6 | 67.8 | 77.9 | 85.9 | 90.9 |

TABLE 23

| Dissolution (Time)-15% Aquacoat® | | | | | | | |
|---|---|---|---|---|---|---|---|
| Time (Days) | Wt (mg) | 1 hr | 2 hr | 4 hr | 8 hr | 12 hrs | 18 hrs | 24 hrs |
| Initial | 210 | 5.4 | 13.9 | 38.0 | 57.8 | 68.4 | 78.6 | 81.3 |
| 28 | 207.3 | 9.5 | 23.8 | 43.4 | 58.8 | 67.8 | 77.0 | 81.3 |

EXAMPLE 8

In Example 8, Hydromorphone beads overcoated with 10% of the Aquacoat® are prepared in accordance with Example 6. The hydromorphone beads of Example 8 have the following formula set forth in Table 24 below:

TABLE 24

| Ingredient | Percent | Amt/Unit |
|---|---|---|
| Hydromorphone beads | 89.3% | 84.2 mg |
| Aquacoat® ECD30 | 8.9% | 8.4 mg |
| Triethyl citrate | 1.8% | 1.7 mg |
| | 100% | 94.3 mg |

To test the effectiveness of curing at a lower relative humidity compared to Example 6, the above beads were cured for 72 hours at 37° C. at 60% relative humidity (rather than 85%RH). Similar initial results were obtained for Example 8 as compared to Example 6, thus indicating that the curing step can also be completed at a lower relative humidity. The results are set forth in Table 25 below:

TABLE 25

| Dissolution (Time)-10% Aquacoat® | | | | | | |
|---|---|---|---|---|---|---|
| Example | 1 hr | 2 hr | 4 hr | 8 hr | 12 hr | 18 hr | 24 hr |
| Ex. 6 | 7.5 | 27.9 | 48.5 | 68.1 | 76.2 | 90.3 | 88.9 |
| Ex. 8 | 1.1 | 18.9 | 45.0 | 65.0 | 76.0 | 85.8 | 91.5 |

EXAMPLES 9–10

Hydromorphone HCl beads were prepared made by spraying a suspension of Hydromorphone HCl and Opadry® Y-5-1442 light pink (20% w/w) onto nu-pariel 18/20 beads, in accordance with the method set forth in Example 1. These beads were then further coated with Opadry® Y-5-1442 light pink (15% w/w). These beads were then further coated with the Surelease® at a level of 10% weight gain. The formula of the coated bead is set forth in Table 26:

TABLE 26

| Ingredient | mg/dose | Percent |
|---|---|---|
| Hydromorphone HCl | 4.0 mg | 4.32% |
| NuPariel beads 18/20 | 74.0 mg | 79.91% |
| Opadry light pink | 6.2 mg | 6.70% |
| Surelease | 8.4 mg | 9.07% |
| | 92.6 mg | 100% |

The batch was then divided into two portions. Example 9 was cured at 60° C./85% RH for 3 days (72 hours), and then dried in a fluid bed dryer for 30 minutes at 60° C. to dry off the excess moisture. These beads were then overcoated with 5% Opadry light pink. Example 10 was left uncured.

Both Examples 9 and 10 were then filled into hard gelatin capsules at a strength of 4 mg hydromorphone per capsule and stored for 3 months at 37° C./100% RH. Dissolution studies were conducted (pursuant to the method set forth for Example 1) initially for both Examples 9 and 10 and again after the 3 month storage at 37° C./100% RH. The results are set forth in Tables 27 and 28 below:

TABLE 27

| | Example 9 | |
|---|---|---|
| Time | Initial | 3 Months at 37° C./100 % RH |
| 1 | 4.7 | 6.5 |
| 4 | 42.3 | 56.0 |
| 8 | 64.9 | 75.0 |
| 12 | 77.2 | 83.19 |

TABLE 28

| | Example 10 | |
|---|---|---|
| Time | Initial | 3 Months at 37° C./100%. RH |
| 1 | 1.6 | 4.5 |
| 4 | 12.0 | 61.9 |
| 8 | 47.8 | 79.0 |
| 12 | 66.7 | 87.7 |

The results indicate that despite the expected differences in initial release rates caused by the use of a different aqueous dispersion of ethylcellulose (Surelease® as compared to Aquacoat®), the curing step as described above for Example 9 still significantly stabilized the product in comparison to the uncured product of Example 10. The relatively faster controlled release rate of the Examples using Aquacoat® as compared to Surelease® may be due to the lesser degree of plasticization during the preparation of the coating formulation. However, products using either coating may be modified to obtain satisfactory results.

EXAMPLE 11

The following example illustrates the stabilization of morphine beads in accordance with the present invention.

A suspension of morphine sulphate and HPMC (Opadry® Clear Y-5-7095) was applied onto 18/20 mesh Nu-pariel beads in a fluid bed granulator with a Wurster insert, at 60° C. A HPMC purple color suspension (Opadry® lavender YS-1-4729) was then applied as an overcoat at the same temperature. The beads were then overcoated to a 5% weight gain with Aquacoat® and triethyl citrate as a plasticizer at 60° C. inlet. The beads were then cured in an oven at 60° C./100% relative humidity for three days. The beads were then dried in the fluid bed granulator at 60° C., and an overcoat of HPMC with a purple color was then applied using the Wuster insert.

The beads were then filled into hard gelatin capsules at a strength of 30 mg morphine sulphate per capsule. The final formula, set forth in Table 29 thus became:

TABLE 29

| Ingredient | mg/capsule | Percent |
|---|---|---|
| Morphine sulphate 5H$_2$O | 30.0 | 8.51% |
| Nu-pariel beads 18/20 | 255.0 | 72.36% |

TABLE 29-continued

| Ingredient | mg/capsule | Percent |
|---|---|---|
| Opadry ® Clear Y-5-7095 | 15.0 | 4.26% |
| Opadry ® Lavender YS-1-4729 | 15.8 | 4.48% |
| Aquacoat ® ECD30 (solids) | 15.8 | 4.48% |
| Triethyl citrate | 3.2 | 0.91% |
| Opadry Lavender Y-S-1-4729 | 17.6 | 4.99% |
| | 352.4 | 100% |

An initial dissolution of the capsules was conducted using the USP paddle method at 100 rpm in 900 ml of water, and again after storage at 37° C./100% relative humidity, and at 60° C. dry for one month. It was observed that a stable product was made. The results are set forth in Table 30:

TABLE 30

| | Percent Morphine Dissolved | | |
|---|---|---|---|
| Time Hrs | Initial | 37° C./100% RH after 1 Mo | 60° C. after 1 Mo |
| 1 | 15.7 | 16.6 | 15.3 |
| 4 | 53.0 | 51.4 | 54.9 |
| 8 | 84.4 | 83.3 | 90.4 |
| 12 | 96.5 | 94.4 | 96.9 |

EXAMPLE 12

A second experiment was conducted with morphine as described in Example 11; however, the retardant Aquacoat® layer was applied to a 15% weight gain to develop a slower releasing morphine product. The final formulation is set forth in Table 31:

TABLE 31

| Ingredient | Mg/capsule | Percent |
|---|---|---|
| Morphine sulphate 5H$_2$O | 30.0 | 7.65% |
| Nu-pariel beads 18/20 | 255.0 | 65.0% |
| Opadry ® Clear Y-5-7095 | 15.0 | 3.82% |
| Opadry ® Lavender YS-1-4729 | 15.8 | 4.03% |
| Aquacoat ® ECD30 (solids) | 47.4 | 12.08% |
| Triethyl citrate | 9.5 | 2.42% |
| Opadry ® Lavender Y-S-1-4729 | 19.6 | 5.00% |
| | 392.3 | 100% |

An initial dissolution of the 30 mg morphine sulphate capsules was conducted as described in Example 10 and again after storage at 37° C./100% relative humidity and 60° C. dry for one month. It was again observed that a stable product was made. The results are set forth in Table 32 below:

TABLE 32

| | Percent Morphine Dissolved | | |
|---|---|---|---|
| Time Hrs | Initial | 37° C./100% RH After 1 Mo | 60° C. After 1 Mo |
| 1 | 0 | 3.1 | 0 |
| 4 | 18.1 | 19.4 | 17.8 |
| 8 | 49.2 | 49.4 | 45.7 |
| 12 | 66.3 | 68.2 | 65.9 |

EXAMPLES 13–14

In Example 13, the applicability of another medicament, theophylline, having very different physical properties compared to hydromorphone is demonstrated.

Theophylline hydrous and colloidal silicon dioxide were first mixed together in a high shear mixer, then sieved using a Jet sieve to enhance flowability. Using a fluid bed granulator equipped with a rotor processor, sugar spheres were layered with the theophylline/colloidal silicon dioxide mixture using a PVP (C-90) solution. Layering was continued until an approximately 78% load was obtained.

The formula of the 400 mg theophylline beads when filled into capsules is set forth in Table 33 as follows:

TABLE 33

|  | Mg/unit capsules |
| --- | --- |
| Theophylline hydrous (equivalent to 400 mg anhydrous theophylline) | 440.0 |
| Colloidal silicon dioxide | 0.4 |
| Sugar spheres 30/35 mesh | 110.0 |
| PVP (C-30) | 13.5 |
|  | 563.9 |

These spheres were then overcoated with a dibutylsebecate plasticized Aquacoat® ECD 30 retardant to a 5% weight gain in the Wurster column in a fluid bed granulator. A portion of the spheres was not cured, and another portion was stored at 60° C. and 100% relative humidity for 72 hours. The following results set forth in Table 34 were obtained:

TABLE 34

|  | 1 hr | 2 hr | 3 hr | 4 hr | 6 hr | 8 hr | 24 hr |
| --- | --- | --- | --- | --- | --- | --- | --- |
| Initial(uncured) | 9.0 | 92.8 | 94.6 | 95.4 | 97.8 | 98.0 | 100.0 |
| 72 hours at 60° C./100% RH | 3.2 | 5.3 | 7.0 | 7.9 | 11.0 | 14.1 | 35.8 |

From the above, it was determined that theophylline spheroids coated with Aquacoat® also are not stable and need to be cured. After storage at 72 hours at 60° C. and 100% relative humidity, a dramatic drop in dissolution rate occurred; however, such conditions may, in some instances, represent "ideal" curing conditions to form a stable product. In view of this goal, the dissolution data after 72 hours at 60%C/100%RH provides a dissolution profile too slow for theophylline.

Therefore, Example 14 was prepared in order to attempt to improve the dissolution profile of the formulation via incorporation of this new curing step, and the coating was altered in order to increase the dissolution rate to 100% theophylline dissolved in 12 hours.

Example 14 was prepared as follows. Theophylline powder layered beads were made as described in Example 13 and were then overcoated with a plasticized Aquacoat® ECD 30 retardant, which, and for this example, included 10% HPMC (hydroxypropyl methyl cellulose). This was done so that the release of theophylline would be faster than Example 13. The inclusion of HPMC to speed up dissolution is known in the prior art. The retardant layer was also coated to a 6% weight gain in the Wurster column of the fluid bed granulator.

The coated beads were then cured for 72 hours at 60° C./100% relative humidity. A dissolution study was conducted initially, and once again after the beads were stored at 37° C./80% relative humidity for three months. It was observed that the stability of the dissolution of the theophylline from the formulation of Example 14 improved dramatically compared to Example 13. It was further observed that by inclusion of HPMC in the retardant layer in the proportions of Aquacoat® ECD 30 (solids):HPMC of 9:1, coated to a 6% weight gain, the dissolution rate of the formulation was increased to 100% theophylline dissolved in 12 hours. The results are set forth in detail in Table 35 below:

TABLE 35

|  | 1 hr | 2 hr | 4 hr | 8 hr | 12 hr |
| --- | --- | --- | --- | --- | --- |
| Cured Initial | 17 | 38 | 68 | 97 | 100 |
| Storage at 37° C./80% RH for 3 months | 13 | 31 | 60 | 94 | 100 |

EXAMPLES 15–17

Controlled Release Hydromorphone HCl 8 mg Formulations—Once-a-Day Preparation

Examples 15–17 were prepared as follows:

1. Drug Loading. Hydromorphone beads were prepared by dissolving hydromorphone HCl in water, adding Opadry Y-5-1442, light pink (a product commercially available from Colorcon, West Point, Pa., which contains hydroxypropyl methylcellulose, hydroxypropyl cellulose, titanium dioxide, polyethylene glycol and D&C Red No. 30 aluminum lake) and mixing for about 1 hour to obtain a 20% w/w suspension. This suspension was then sprayed onto NuPareil 18/20 mesh beads using a Wurster insert.

2. First Overcoat. The loaded hydromorphone beads were then overcoated with a 5% w/w gain of Opadry Light Pink using a Wurster insert. This overcoat was applied as a protective coating and provides immediate release hydromorphone beads. See Table 36 below:

TABLE 36

| Immediate Release Beads | | | |
| --- | --- | --- | --- |
| Processing Step | Ingredient | % | mg per Unit |
| Drug Loading | Hydromorphone HCl | 4.7 | 4.0 |
|  | Nu-Pareil 18/20 | 87.9 | 74.0 |
|  | Opadry Lt Pink | 2.4 | 2.0 |
| First Overcoat | Opadry Lt Pink | 5.0 | 4.2 |
| Total |  | 100.0 | 84.2mg |

3. Retardant Coat. After the first overcoat, the hydromorphone beads were then coated with a retardant coating of Aquacoat ECD 30 and Triethyl Citrate (a plasticizer) to a 5%, 10% and 15% weight gain (based on dry wt. of Aquacoat). A Wurster insert was used to apply the coating suspensions.

4. Curing. After the application of the retardant coating, the beads were placed in a 60° C. oven containing a tray of water to maintain about a 100% relative humidity level. All three batches were allowed to cure for 72 hours.

5. Second Overcoat. The cured beads were removed from the humid oven, and dried in a fluid bed dryer for about one hour. The dried cured beads were then overcoated with a 5% w/w gain of Opadry Light Pink using a Wurster insert. This overcoat was applied as a protective coating. The final formulations for beads having 5%, 10%, and 15% Aquacoat coatings are set forth in Tables 37, 38 and 39 below, respectively:

TABLE 37

| Beads with 5% Coating | | | |
|---|---|---|---|
| Processing Step | Ingredient | % | mg per Unit |
| Drug Loading | Hydromorphone HCl | 4.2 | 4.0 |
| | Nu-Pareil 18/20 | 78.8 | 74.0 |
| | Opadry Lt Pink | 2.1 | 2.0 |
| First Overcoat | Opadry Lt Pink | 4.5 | 4.2 |
| Retardant Coat | Aquacoat | | |
| | ECD 30 (dry wt.) | 4.5 | 4.2 |
| | Triethyl Citrate | 0.9 | 0.8 |
| Second Overcoat | Opadry Lt Pink | 5.0 | 4.7 |
| Total | | 100.0 | 93.9mg |

TABLE 38

| Beads with 10% Coating | | | |
|---|---|---|---|
| Processing Step | Ingredient | % | mg per Unit |
| Drug Loading | Hydromorphone HCl | 4.0 | 4.0 |
| | Nu-Pareil 18/20 | 74.5 | 74.0 |
| | Opadry Lt Pink | 2.0 | 2.0 |
| First Overcoat | Opadry Lt Pink | 4.2 | 4.2 |
| Retardant Coat | Aquacoat | | |
| | ECD 30 (dry wt.) | 8.5 | 8.4 |
| | Triethyl Citrate | 1.7 | 1.7 |
| Second Overcoat | Opadry Lt Pink | 5.1 | 5.0 |
| Total | | 100.0 | 99.3mg |

TABLE 39

| Beads with 15% Coating | | | |
|---|---|---|---|
| Processing Step | Ingredient | % | mg per unit |
| Drug Loading | Hydromorphone HCl | 3.8 | 4.0 |
| | Nu-Pareil 18/20 | 70.8 | 74.0 |
| | Opadry Lt Pink | 1.9 | 2.0 |
| First Overcoat | Opadry Lt Pink | 4.0 | 4.2 |
| Retardant Coat | Aquacoat | | |
| | ECD 30 (dry wt.) | 12.1 | 12.6 |
| | Triethyl Citrate | 2.4 | 2.5 |
| Second Overcoat | Opadry Lt Pink | 5.0 | 5.2 |
| Total | | 100.0 | 104.5mg |

7. Encapsulation. The hydromorphone beads were then filled into hard gelatin capsules to a total of 8 mg Hydromorphone HCl per capsule using the following combinations:

Example 15: All beads have 5% Aquacoat coating;

Example 16: 75% beads having 10% Aquacoat coating and 25% immediate release beads;

Example 17: 75% beads having 15% Aquacoat coating and 25% immediate release beads.

Dissolution studies were conducted on the Aquacoat-coated hydromorphone beads of Examples 15–17 both initially and after 28 days. The results are set forth in Tables 40–42 below:

TABLE 40

| Dissolution of Example 15 | | | | | | | |
|---|---|---|---|---|---|---|---|
| | Time | | | | | | |
| | 1 hr | 2 hr | 4 hr | 8 hr | 12 hr | 18 hr | 24 hr |
| Initial | 33.8 | 54.6 | 71.2 | 85.7 | 92.9 | 97.3 | 99.9 |
| 28 days | 34.0 | 53.1 | 70.8 | 86.1 | 93.1 | 98.2 | 100.7 |

TABLE 41

| Dissolution of Example 16 | | | | | | | |
|---|---|---|---|---|---|---|---|
| | Time | | | | | | |
| | 1 hr | 2 hr | 4 hr | 8 hr | 12 hr | 18 hr | 24 hr |
| Initial | 31.6 | 43.4 | 59.2 | 72.3 | 79.2 | 85.7 | 90.3 |
| 28 days | 32.3 | 43.7 | 59.2 | 72.6 | 80.7 | 86.8 | 91.5 |

TABLE 42

| Dissolution of Example 17 | | | | | | | |
|---|---|---|---|---|---|---|---|
| | Time | | | | | | |
| | 1 hr | 2 hr | 4 hr | 8 hr | 12 hr | 18 hr | 24 hr |
| Initial | 29.3 | 37.2 | 52.1 | 66.4 | 73.9 | 80.4 | 85.4 |
| 28 days | 31.1 | 37.0 | 51.4 | 66.0 | 73.7 | 81.3 | 86.2 |

Stability studies of the Aquacoat-coated hydromorphone beads of Examples 15 –17, as set forth above, show the initial dissolutions to be the same as dissolutions done on samples placed at 37° C./80% RH conditions.

EXAMPLES 18–20

In Examples 18–20, a single dose six-way randomized crossover study (one week wash-out) was conducted in 12 patients and compared to the results obtained with an equivalent dose of an immediate release preparation. Blood samples were taken initially, 0.25, 0.5, 0.75, 1, 1.5, 2, 2.5, 3, 3.5, 4, 6, 8, 10, 12, 18, 24, 30, 36 and 48 hours after administration in order to determine plasma levels. Comparative Example 18A is 8 mg of a hydromorphone immediate release formulation (two tablets of Dilaudid® 4 mg tablets, commercially available from Knoll). Example 18 is an 8 mg dose of the encapsulated hydromorphone beads of Example 15. Example 19 is an 8 mg dose of the encapsulated hydromorphone beads of Example 16. Example 20 is an 8 mg dose of the encapsulated hydromorphone beads of Example 17.

Figure 7:
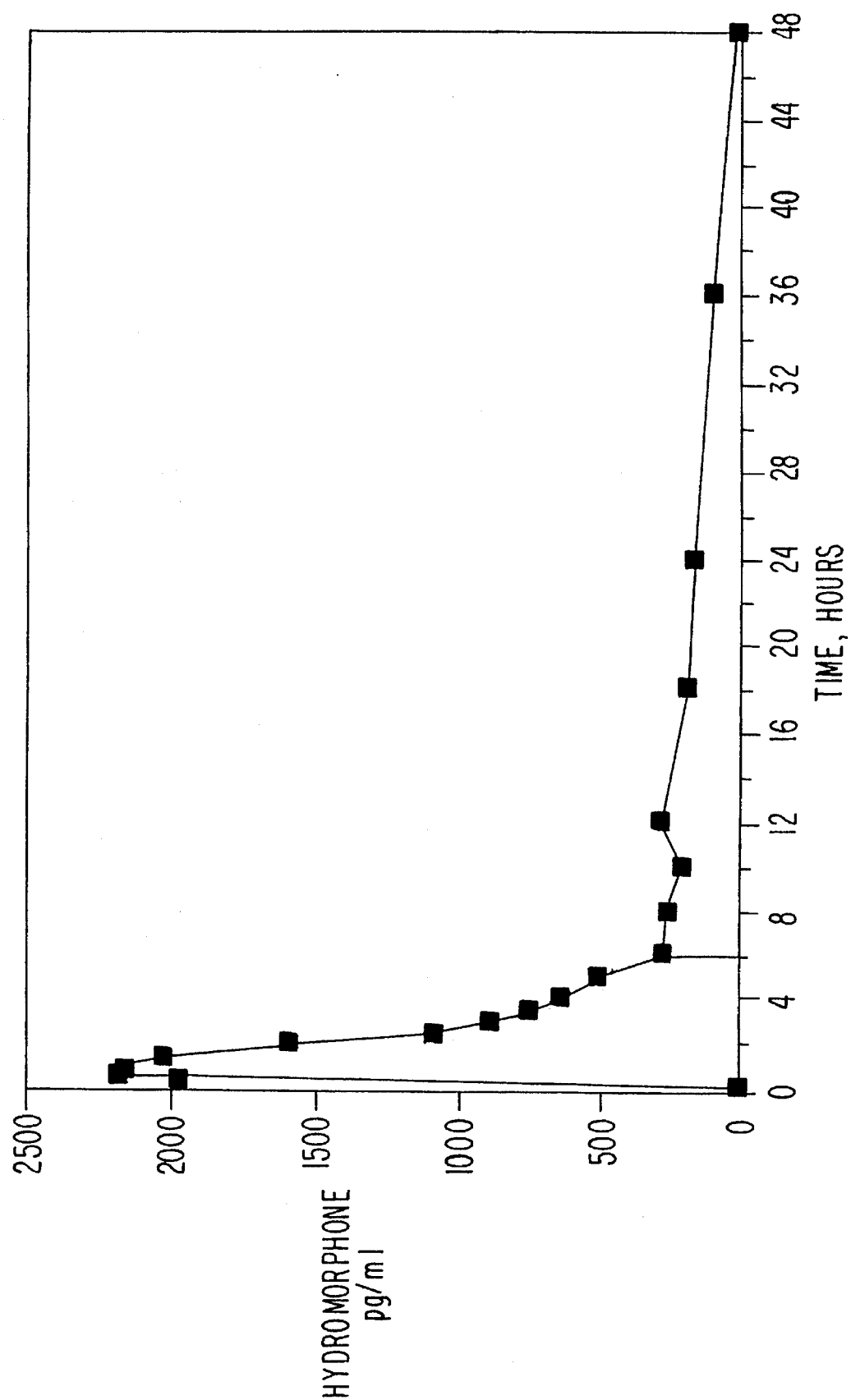
FIG. 7 is a graphical representation of the results obtained for Comparative Example 18A.
Figure 8:
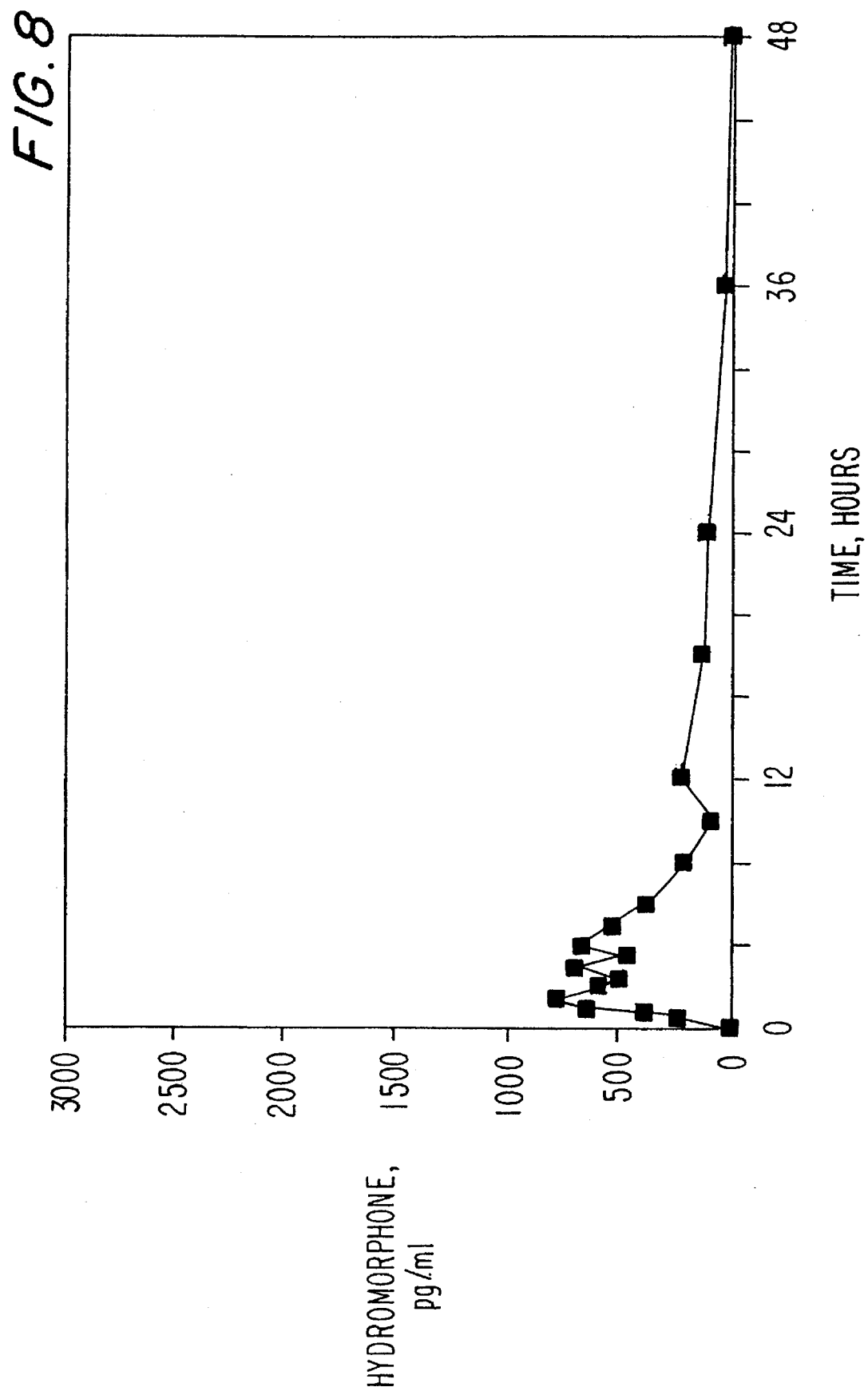
FIG. 8 is a graphical representation of the results obtained for Example 18.
Figure 9:
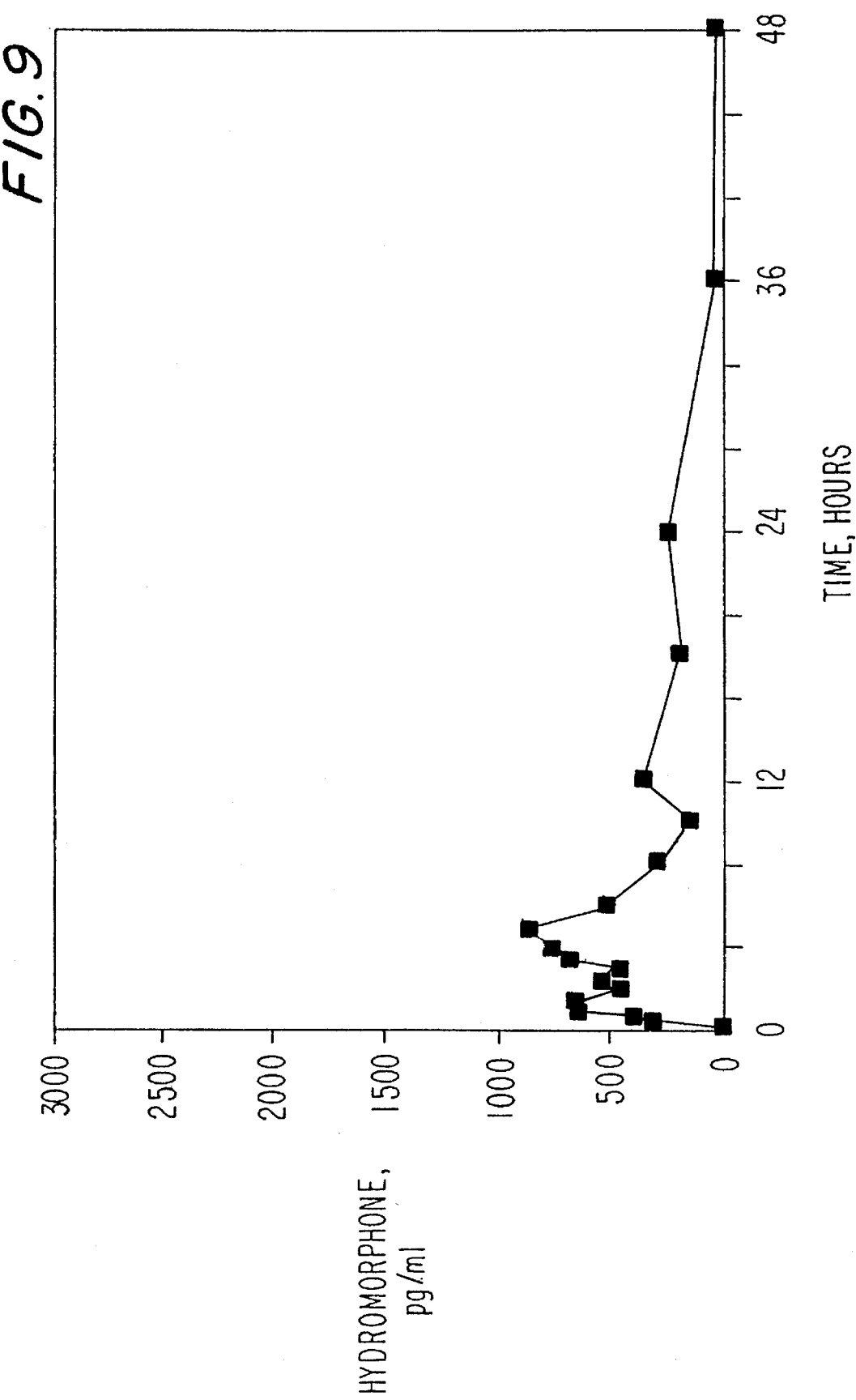
FIG. 9 is a graphical representation of the results obtained for Example 19.
Figure 10:
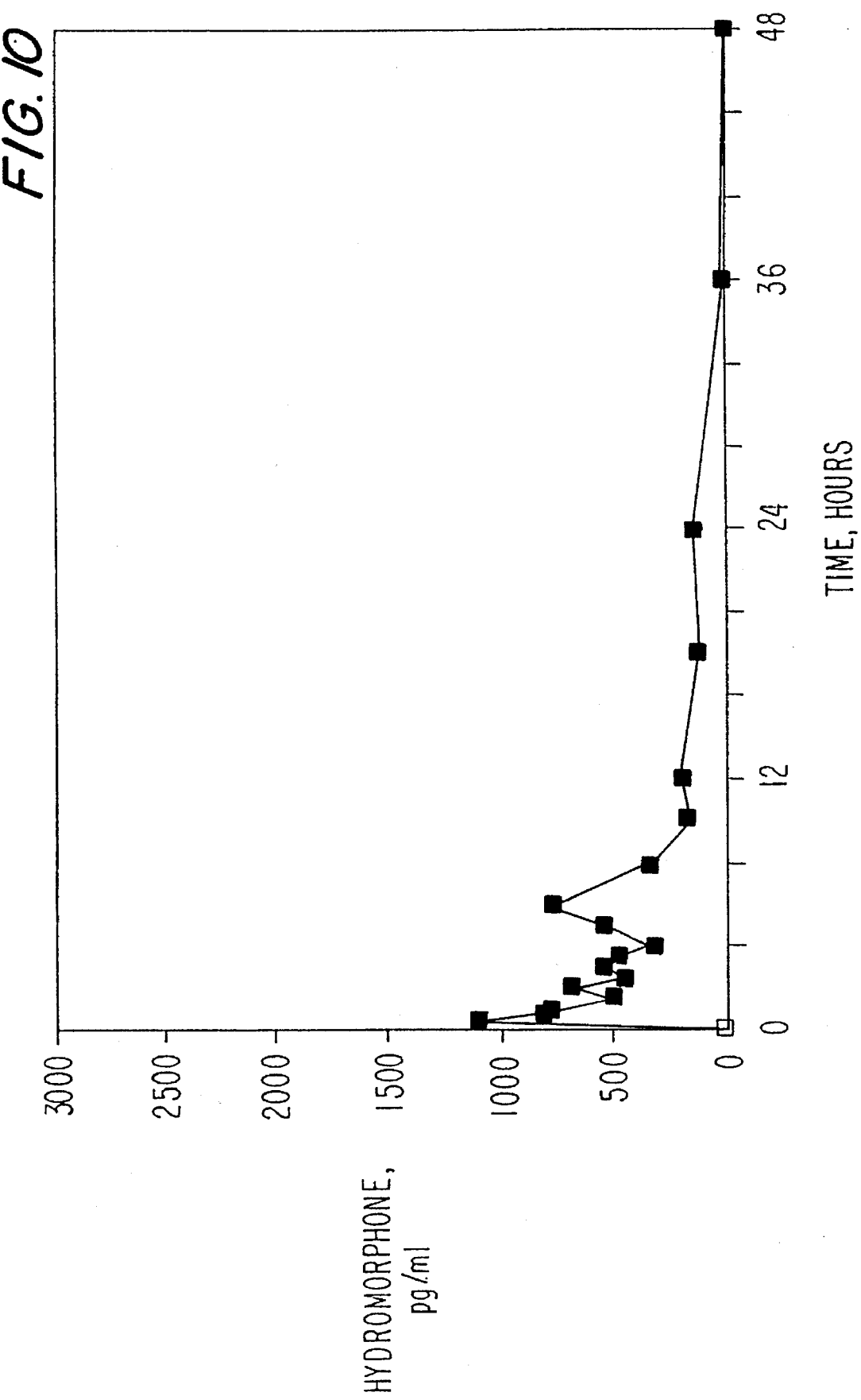
FIG. 10 is a graphical representation of the results obtained for Example 21.

The results obtained for Comparative Example 18A are set forth in FIG. 7. The results obtained for Example 18 are set forth in FIG. 8. The results obtained for Example 19 are set forth in FIG. 9. The results obtained for Example 20 are set forth in FIG. 10. The results for Examples 18–20 are further set forth in Table 43 below, which provides data regarding area under the curve (bioavailability), the peak plasma concentration ($C_{max}$), and the time to reach peak plasma concentration ($t_{max}$).

TABLE 43

| Product | AUC | Cmax | Tmax |
|---|---|---|---|
| Comparative Example 18A 2 Dilaudid Tablets | 12427 | 3013 | 1.10 |
| Example 18 | 6718 | 1070 | 2.58 |
| Example 19 | 9933 | 1265 | 2.39 |
| Example 20 | 8695 | 1138 | 0.88 |

Dilaudid is known to be effective for about 6 hours. Blood levels for 8 mg Dilaudid at 6 hours were about 300 pg/ml hydromorphone. Therefore, a circulating concentration of about 300 pg/ml should be an effective analgesic concentration in the blood.

The results obtained for Example 19 showed that at the 12th hour after administration, the blood levels of hydromorphone were over 500 pg/ml hydromorphone, and at the 24th hour after administration, the blood levels were well over 300 pg/ml. Therefore, this product is considered to be suitable for once a day administration.

Example 20, on the other hand, provided levels of over 300 pg/ml at the 12th hour after administration, with levels of about 250 pg/ml at the 24th hour after administration. Therefore, this product is considered to be suitable for twice a day administration, and possibly suitable for once a day administration.

EXAMPLE 21

In Example 21, morphine sulfate controlled release beads with a 5% w/w controlled release of which 7% of the coating includes HPMC as a pore former are prepared as follows.

First, a starting bead product is manufactured using a rotor processing technique. The base morphine sulfate bead formula to which the controlled release coating is applied to is set forth in Table 44 below:

TABLE 44

| Ingredient | Amt/Unit |
|---|---|
| Morphine Sulfate Powder | 30 mg |
| Lactose Hydrous Impalpable | 42.5 mg |
| PVP | 2.5 mg |
| Sugar Beads 18/20 | 125 mg |
| Purified Water | qs |
| Opadry Red YS-1-1841 | 10.5 mg |
| Total | 210.5 mg |

The controlled release coating is manufactured as follows. The pore former Methocel E5 Premium (HPMC), is dispersed and dissolved in enough purified water to yield a 2% w/w solution.

An Aquacoat dispersion is plasticized with triethyl citrate for approximately 30 minutes. After 30 minutes the HPMC dispersion is mixed into the plasticized Aquacoat dispersion, and blended for an additional 15–30 minutes. A load of the morphine sulfate beads is charged into a Uniglatt Wurster Insert equipped with a 1.2 mm fluid nozzle. The beads are then filmcoated with the Aquacoat/HPMC dispersion (in a ratio of 93:7) to a weight gain of 5%.

The controlled release coating formula used in Example 21 is set forth in Table 45 below:

TABLE 45

| Ingredient | Amt/Unit |
|---|---|
| Morphine Sulfate Base Beads | 210.5 mg |
| Aquacoat ECD 30 (solids) | 9.8 mg |
| Methocel E5 Premium | 0.7 mg |
| Triethyl Citrate | 2.1 mg |
| Purified Water | qs |
| Opadry Red YS-1-1841 | 11.7 mg |
| Purified Water qs | |
| Total | 234.8 mg |

After completion of the controlled release coating process, the coated beads are discharged from the Wurster Insert into a curing tray and cured in a temperature/humidity chamber at 60° C./80% RH for 72 hours. Upon completion of this curing step, the beads are dried to a LOD of 4% or less and are given a final overcoat of Opadry Red YS-1-1841 (15% w/w solution) using the Uniglatt Wurster Insert. The beads are then filled into hard gelatin capsules using a capsule filling machine to obtain the finished product.

The finished product is then subjected to dissolution testing via USP Apparatus II (paddle method), 100 rpm, 37° C., 700 ml simulated gastric fluid (without enzyme) for one hour, and then 900 ml simulated gastric fluid (without enzymes) after first hour.

The finished product is also subjected to dissolution testing after being stored for 3 months and 6 months at room temperature; as well as under accelerated storage conditions (40° C./75% RH) for one month, two months and three months. The results are set forth in Table 46 below:

TABLE 46

Morphine Sulfate 30 mg Capsules
5% Controlled Release Coating 93:7 Ratio

| Storage Conditions & Testing Time | Morphine Sulfate 5H$_2$O mg/cap | Dissolution | | | | | | |
|---|---|---|---|---|---|---|---|---|
| | | 1 Hour | 2 Hour | 4 Hour | 8 Hour | 12 Hour | 18 Hour | 24 Hour |
| Initial RT | 29.75 | 25.9 | 42.7 | 71.1 | 96.8 | 105.3 | 105.6 | 107.0 |
| 3 months | 29.63 | 25.0 | 41.2 | 68.2 | 93.0 | 102.7 | | |
| 6 months | 29.64 | 22.8 | 40.4 | 65.7 | 91.5 | 102.9 | | |
| 40° C./75% RH | | | | | | | | |
| 1 month | 29.33 | 21.9 | 39.1 | 65.9 | 92.9 | 103.0 | | |
| 2 months | 29.76 | 23.1 | 39.2 | 67.4 | 93.3 | 103.3 | | |
| 3 months | 29.16 | 21.5 | 37.6 | 67.5 | 92.8 | 109.2 | | |

As can be seen from the dissolution results provided in Table 46, the capsules of Example 21 provide a stable dissolution profile even after exposure to accelerated conditions for 3 months.

EXAMPLE 22

In Example 22, morphine sulfate controlled release beads with a controlled release coating of 5% w/w (including 5% HPMC as a pore former, by weight of the coating), is prepared.

A batch of approximately 892.4 g of morphine sulfate controlled release beads is manufactured with a 5% w/w controlled release coating and a 5% HPMC overcoat. The morphine sulfate bead formula to which the controlled release coating is applied are prepared as described in Example 21. Thereafter, the controlled release coating is prepared and applied to the beads. Further information concerning the formulation of Example 22 is provided in Table 47 below:

TABLE 47

| Ingredient | Amt/Unit |
| --- | --- |
| Morphine Sulfate Base Beads | 210.5 mg |
| Aquacoat ECD 30 (solids) | 10.0 mg |
| Methocel E5 Premium | 0.5 mg |
| Triethyl Citrate | 2.1 mg |
| Purified Water qs | |
| Opadry Red YS-1-1841 | 11.7 mg |
| Purified Water qs | |
| Total | 234.8 mg |

The manufacturing process and curing and encapsulation technique used is the same for Example 22 as per Example 21, the difference being that the morphine sulfate beads are filmcoated with an Aquacoat/HPMC (95:5) dispersion in Example 22.

The results of dissolution testing conducted in the same manner as per Example 21 are set forth in Table 48 below:

TABLE 48

Morphine Sulfate 30 mg Capsules
5% Controlled Release Coating 95:5 Ratio

| Storage Conditions & Testing Time | Morphine Sulfate 5H₂O mg/cap | Dissolution | | | | | | |
| --- | --- | --- | --- | --- | --- | --- | --- | --- |
| | | 1 Hour | 2 Hour | 4 Hour | 8 Hour | 12 Hour | 18 Hour | 24 Hour |
| Initial RT | 30.38 | 16.9 | 29.6 | 52.3 | 79.8 | 92.8 | 101.4 | 104.7 |
| 30° C. | | | | | | | | |
| 3 months | 30.20 | 14.5 | 28.2 | 50.4 | 77.2 | 90.3 | | |
| 6 months | 30.3 | 15.7 | 28.9 | 49.7 | 78.6 | 92.1 | | |
| 40° C./ 75% RH | | | | | | | | |
| 1 month | 29.84 | 15.9 | 27.1 | 47.7 | 73.8 | 87.4 | | |
| 2 months | 30.72 | 15.5 | 27.4 | 49.6 | 76.6 | 89.0 | | |
| 3 months | 29.95 | 13.9 | 27.4 | 49.8 | 76.6 | 88.9 | | |

As can be seen from the dissolution results provided in Table 48, the capsules of Example 22 provide a dissolution which is slower than that of Example 21. The capsules once again provide a stable dissolution profile despite exposure to accelerated conditions.

EXAMPLE 23

In Example 23, morphine sulfate controlled release beads with a controlled release coating of 5% w/w (including 3% HPMC as a pore former, by weight of the coating), are prepared.

A batch of approximately 892.4 g of morphine sulfate controlled release beads is manufactured with a 5% w/w controlled release coating and a 5% HPMC overcoat. The morphine sulfate beads to which the controlled release coating was applied are prepared as described in Example 21. Thereafter, the controlled release coating is prepared and applied to the beads to a weight gain of 5%. Further information concerning the formulation of Example 23 is provided in Table 49 below:

TABLE 49

| Ingredient | Amt/Unit |
| --- | --- |
| Morphine Sulfate Base Beads | 210.5 mg |
| Aquacoat ECD 30 (solids) | 10.2 mg |
| Methocel E5 Premium | 0.3 mg |
| Triethyl Citrate | 2.1 mg |
| Purified Water qs | |
| Opadry Red YS-1-1841 | 11.7 mg |
| Purified Water qs | |
| Total | 234.8 mg |

The manufacturing process and curing and encapsulation technique used is the same for Example 23 as per Example 21, the difference being that the beads are filmcoated with an Aquacoat/HPMC (97:3) dispersion in Example 23.

The results of dissolution testing conducted in the same manner as per Example 21 are set forth in Table 50 below:

TABLE 50

MSCR 30 mg 5% CCI (Ratio of 97:3) Capsules

| Specifications Storage Conditions & Testing Time | Morphine Sulfate 5H₂O 30 mg/cap | Dissolution | | | | | |
| --- | --- | --- | --- | --- | --- | --- | --- |
| | | 1 Hour | 2 Hour | 4 Hour | 8 Hour | 12 Hour | 24 Hour |
| Initial | | 17.8 | 28.4 | 46.7 | 73.1 | 86.0 | 99.0 |
| RT 30° C./60% RH 3 months | 31.60 mg/cap | 17.9 | 27.3 | 44.6 | 71.1 | 86.0 | 99.8 |
| 40° C./75% RH | 28.0 | | | | | | |
| 1 month | 25.64 mg | 18.3 | 26.4 | 46.9 | 77.0 | 92.9 | 109.7 |
| 2 months | 29.83 mg | 17.1 | 29.3 | 47.2 | 75.8 | 92.4 | 104.7 |

TABLE 50-continued

MSCR 30 mg 5% CCI (Ratio of 97:3) Capsules

Specifications

| Storage Conditions & Testing | Morphine Sulfate 5H$_2$O | Dissolution | | | | | |
|---|---|---|---|---|---|---|---|
| Time | 30 mg/cap | 1 Hour | 2 Hour | 4 Hour | 8 Hour | 12 Hour | 24 Hour |
| 3 months | 31.63 mg | 14.3 | 23.9 | 40.8 | 67.2 | 81.1 | 96.3 |

As can be seen from the dissolution results provided in Table 50, the capsules of Example 23 provide a dissolution which is slower than that of Example 22. The capsules once again provide a stable dissolution profile despite exposure to accelerated conditions.

EXAMPLE 24

Human bioavailability studies were conducted to compare the 30 mg morphine sulfate controlled release capsules produced in Examples 21 and 22 to a reference standard, MS Contin 30 mg tablets, which are marketed commercially for twice-a-day administration. The study was a three-way crossover study using normal male volunteers with a one week wash-out period with the doses being administered under fasting conditions. Fifteen (15) volunteers completed the study.

A summary of the results obtained in this study are set forth in Table 51 below:

TABLE 51

| Measurement | MS Contin | Example 21 | Example 22 |
|---|---|---|---|
| AUC | 89.31 | 96.24 | 93.85 |
| T$_{max}$ | 2.62 | 2.90 | 3.87 |
| C$_{max}$ | 10.09 | 7.02 | 5.89 |
| PW@HH* | 5.25 | 9.00 | 10.50 |

*Peak Width at Half-Height

Figure 11:
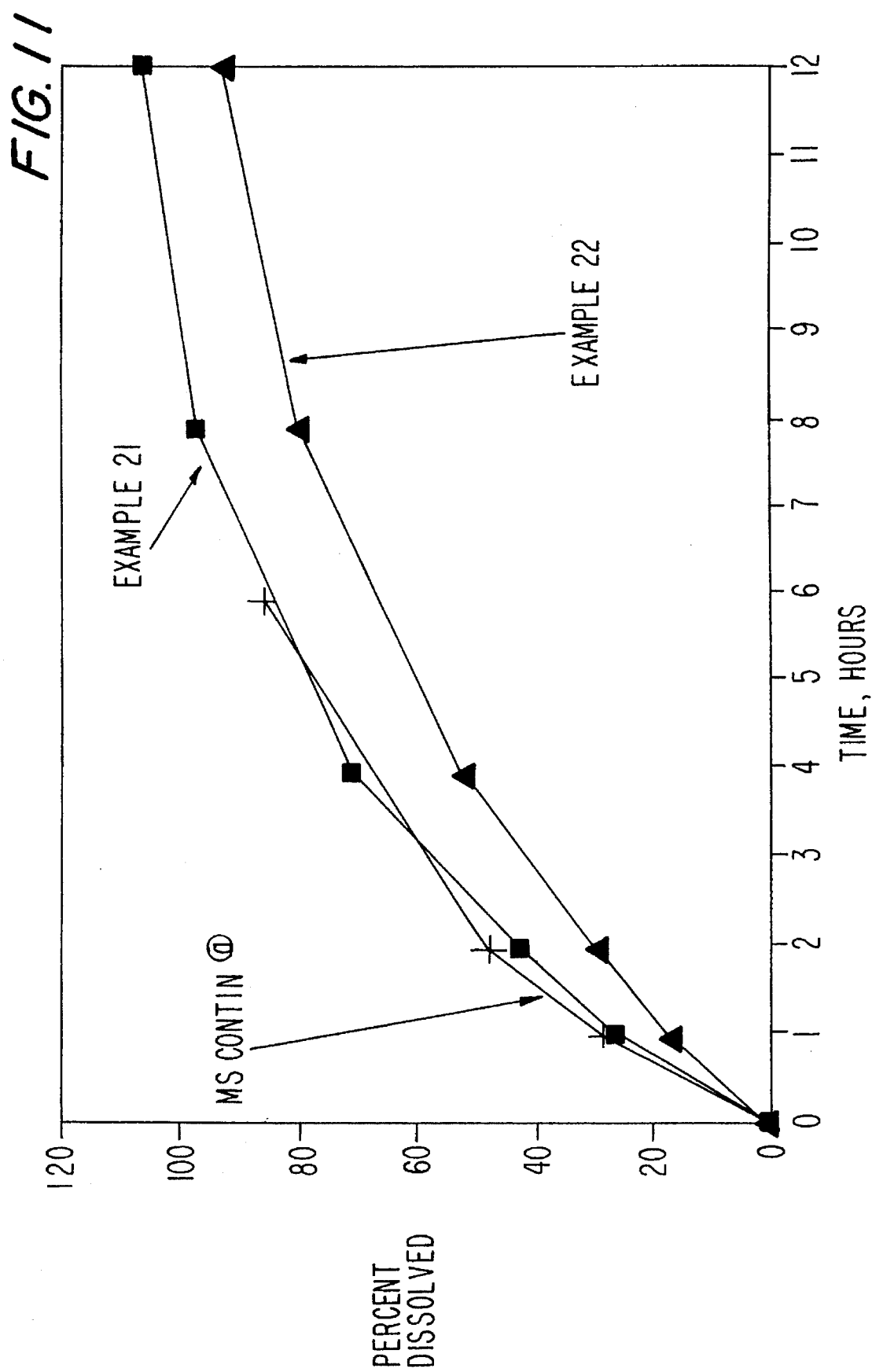
FIG. 11 is a graphical representation comparing the in-vitro release of Examples 22 and 23 versus a commercially available reference (MS Contin)
Figure 12:
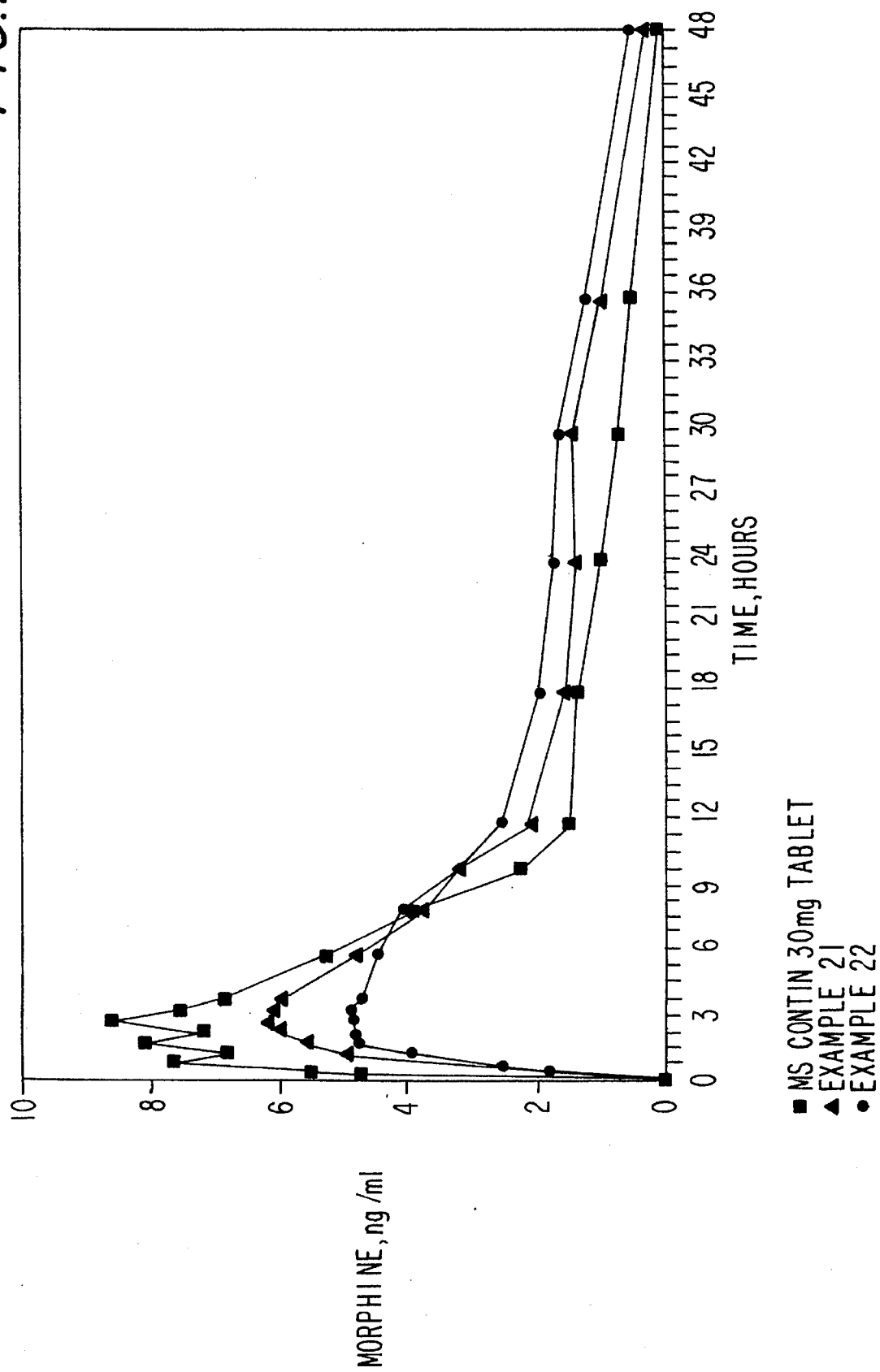
FIG. 12 is a graphical representation of the blood levels obtained for the controlled release formulation of Examples 22 and 23 versus a commercially available reference (MS Contin)

FIG. 11 is a graphical representation of the in-vitro percent dissolved of each of the formulations (MS Contin, Example 21 and Example 22). FIG. 12 is a graphical representation of the blood levels obtained in the volunteers for each of the formulations.

Figure 13:
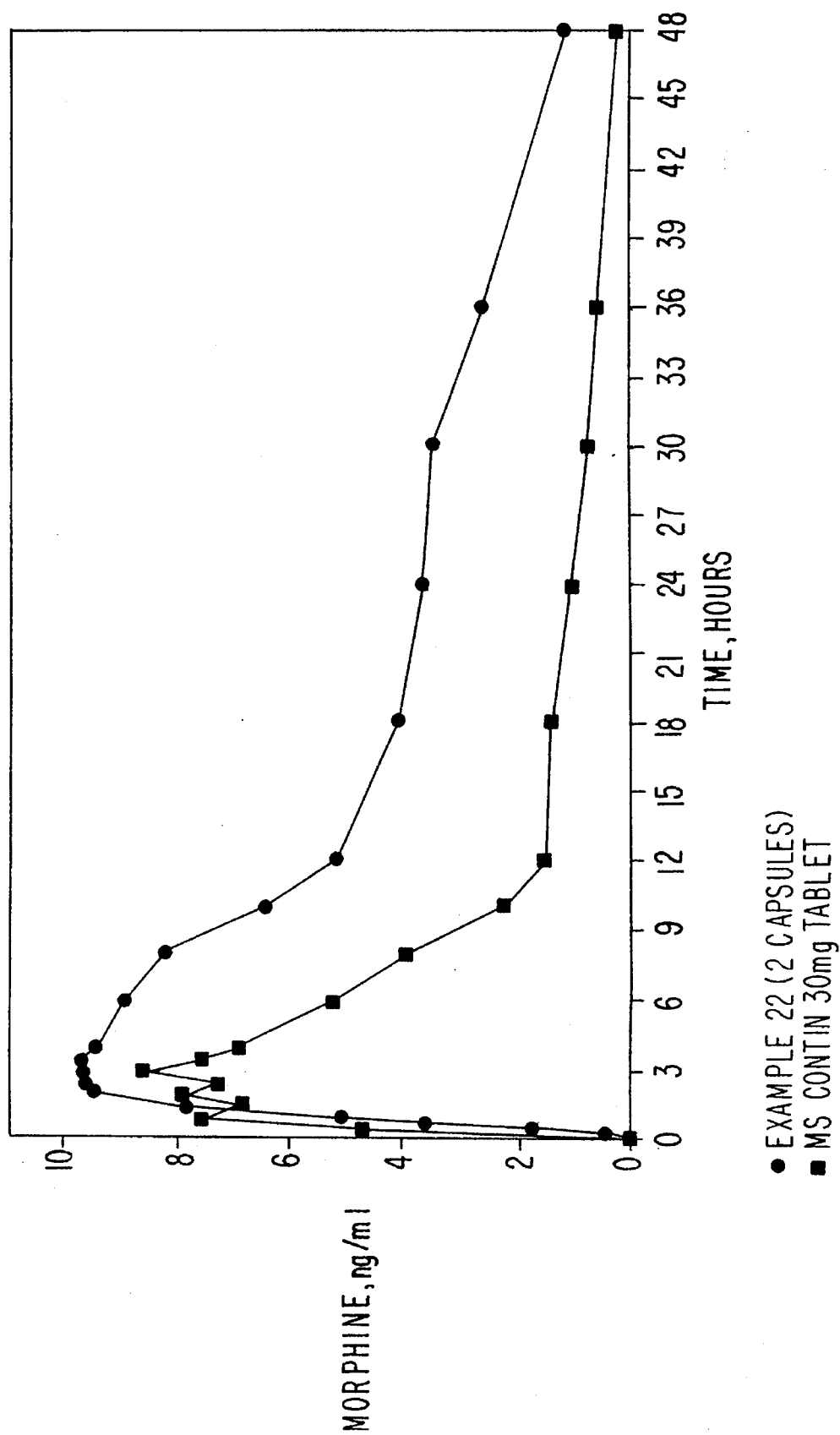
FIG. 13 is a graphical representation of the blood levels obtained when two 30 mg capsules of Example 23 are administered, in comparison to one 30 mg MS Contin tablet.

FIG. 13 is a plot of the blood level curve obtained with MS Contin to a theoretical blood level curve which would be obtained if two 30 mg morphine sulfate controlled release capsules of Example 22 (ratio of Aquacoat/HPMC is 95:5) are administered simultaneously. The theoretical plot of Example 22 (wherein the blood level obtained with one capsule of Example 22 is doubles at each time point) indicate that the capsules of Example 22 appear suitable for administration to human patients on a once-a-day basis. This is a most surprising result because the in-vitro dissolution tests appeared to indicate that the formulation would be suitable only for twice-a-day administration (see FIG. 11 showing in-vitro dissolution curves).

EXAMPLE 25

From the data in Example 24, it was apparent that the capsules of Example 22 (in which the beads are coated with a 5% coating of Aquacoat (HPMC in a 95:5% ratio)) gave blood profiles that looked suitable for once-a-day administration. However, the data indicated that with a slight decrease in the quantity of pore former (HPMC), an even better dosage formulation for a once-a-day product might be obtained. Therefore, a human bioavailability study was conducted using the capsule produced in Example 23 which contained a 3% pore former with the capsules of Example 22 and MS Contin 30 mg as the reference. In the same study the effect of dosing with food was also investigated. Table 52 provides a summary of the results obtained.

TABLE 52

| Study Group | AUC | T$_{max}$ | C$_{max}$ |
|---|---|---|---|
| Ex. 24 (97:3 Fasted) | 101 | 5.6 | 5.9 |
| Ex. 28 (95:5 Fasted) | 93 | 3.6 | 7.0 |
| Ex. 24 (97:3 Fed) | 96 | 7.8 | 5.9 |
| MS Contin (Fasted) | 103 | 2.3 | 13.0 |

Figure 14:
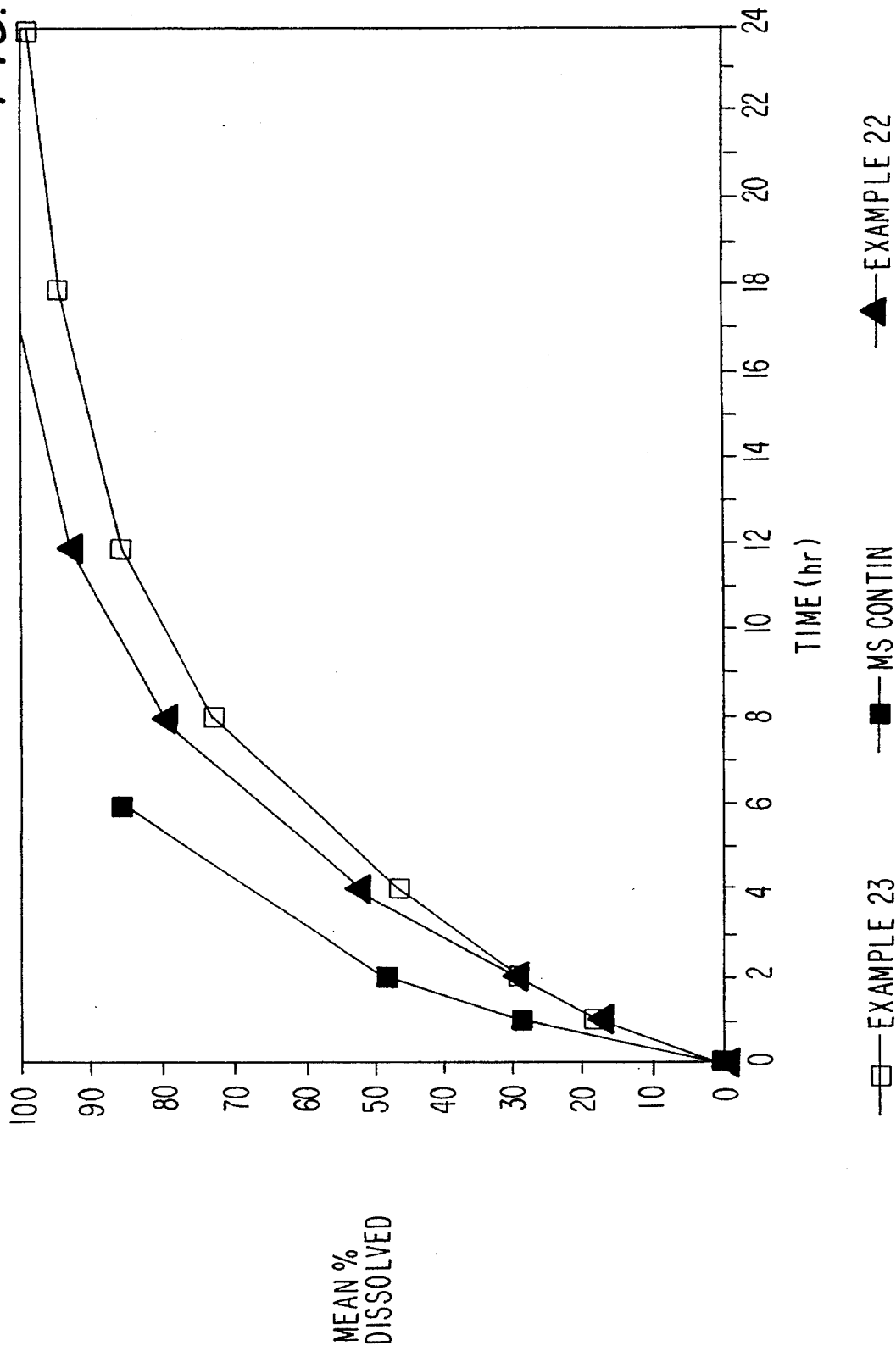
FIG. 14 is a graphical representation comparing the in-vitro release of Examples 23 and 24 versus MS Contin.

FIG. 14 provides comparative in-vitro dissolution curves obtained with Example 23, Example 22 and MS Contin.

Figure 15:
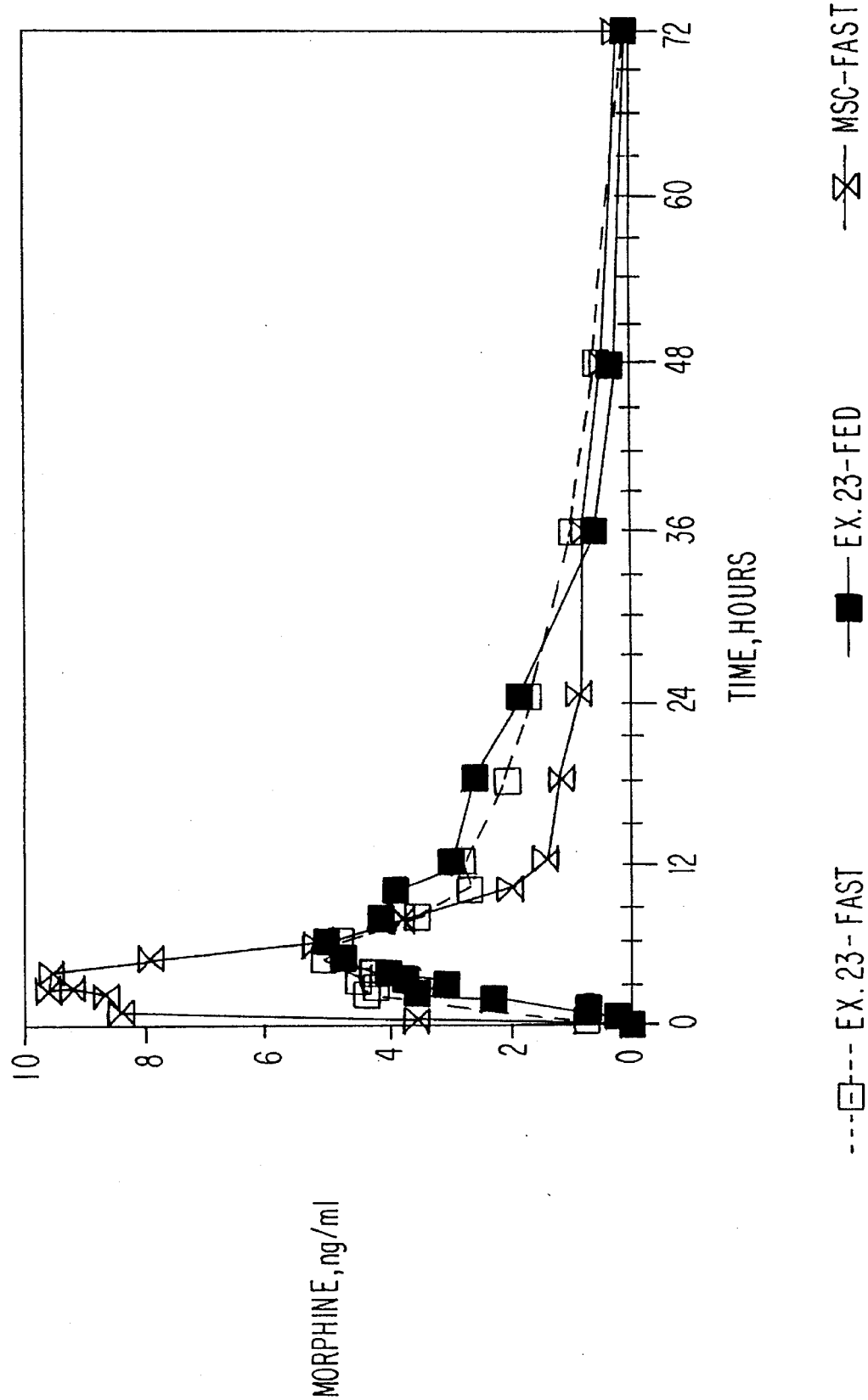
FIG. 15 is a graphical representation of the blood levels obtained for Examples 23 and 24 versus MS Contin.

FIG. 15 provides representative blood levels obtained after administration of Example 23 (both fed and fasted) versus MS Contin (fasted).

Figure 16:
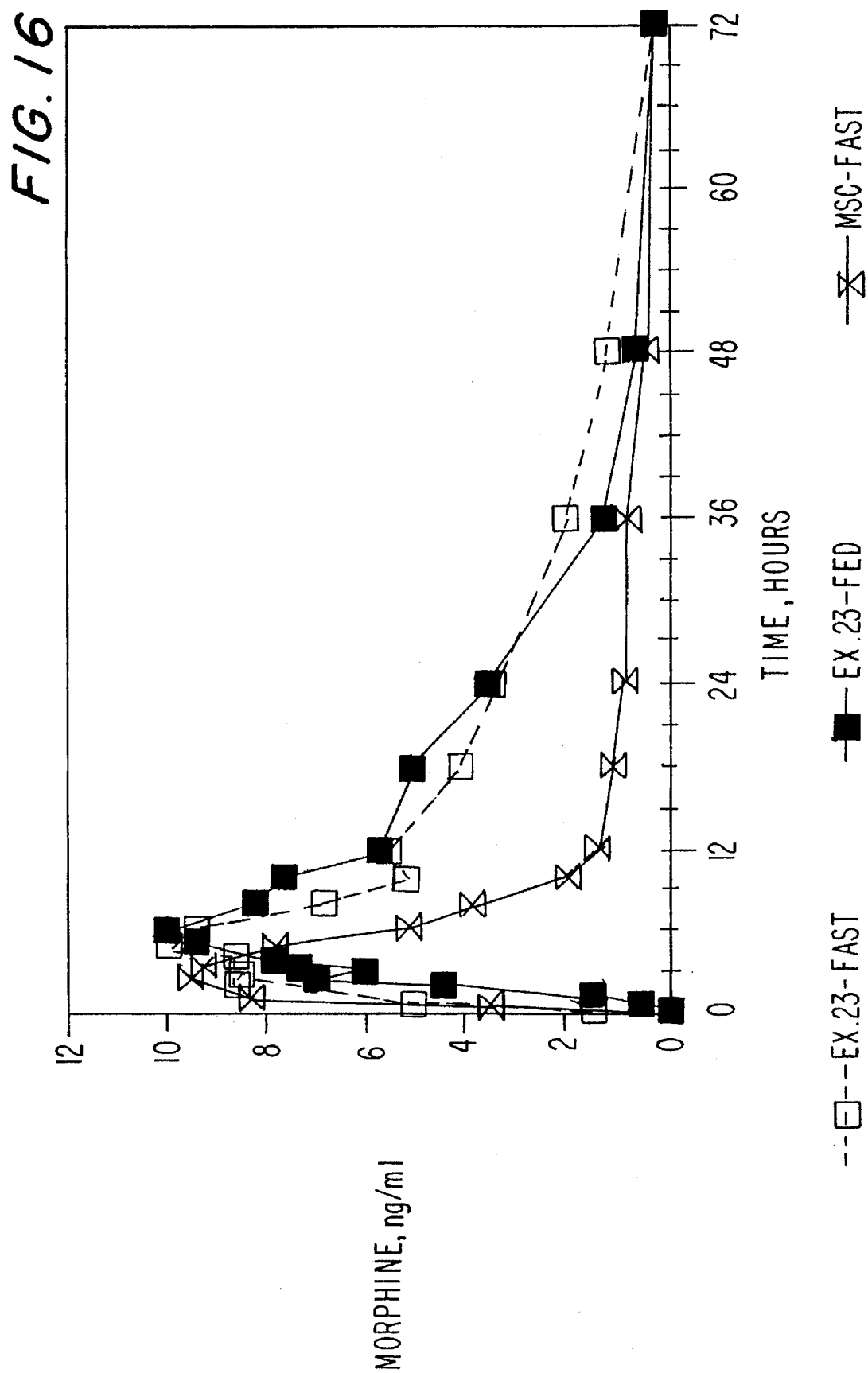
FIG. 16 is a graphical representation of the blood levels obtained when two 30 mg capsules of Example 24 are administered at the same time, in comparison to one 30 mg MS Contin tablet.
Figure 17:
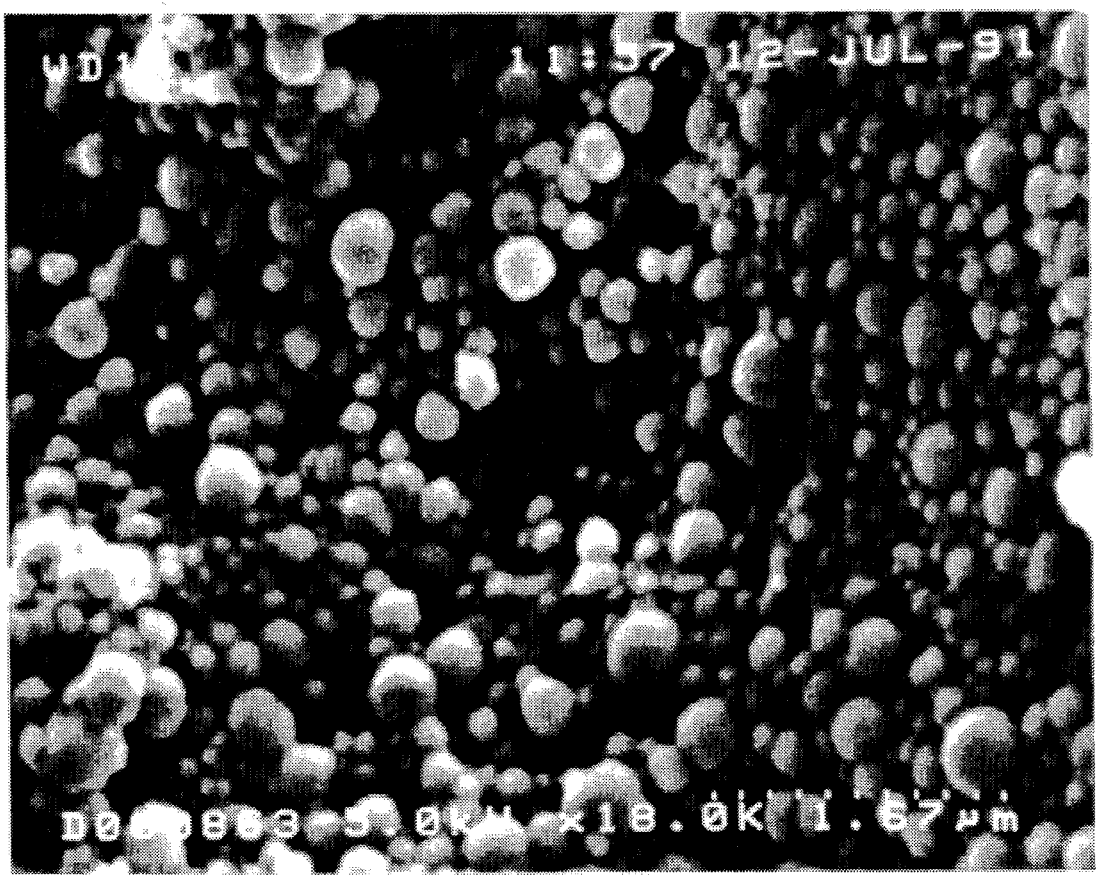
FIG. 17 is a SEM of a pharmaceutical bead coated with the controlled release coating of the present invention prior to curing.
Figure 18:
FIG. 18 is an SEM of the coated bead depicted in FIG. 17 after curing in accordance with the present invention.

FIG. 16 is a plot of the blood level curve obtained with MS Contin to a theoretical blood level curve which would be obtained if two 30 mg morphine sulfate controlled release capsules of Example 23 (ratio of Aquacoat/HPMC is 95:5) are administered simultaneously. The theoretical plot of Example 23 (wherein the blood level obtained with one capsule of Example 23 is doubles at each time point) indicate that the capsules of Example 23 appear suitable for administration to human patients on a once-a-day basis. This is a most surprising result because the in-vitro dissolution tests appeared to indicate that the formulation would be suitable only for twice-a-day administration (see FIG. 11 showing in-vitro dissolution curves).

EXAMPLE 26

Controlled release acetaminophen (APAP) controlled release tablets are prepared in accordance with the present invention as follows. First, immediate release APAP cores are prepared by compressing Compap coarse L into tablet cores weighing approximately 555.6 mg. Compap coarse L contains approximately 90% APAP, along with pharmaceutical grade excipients including a binder, disintegrant and lubricant, and is a directly compressible material commercially available from Mallinckrodt, Inc., St. Louis, Mo. The APAP tablet cores include approximately 500 mg of APAP. The compap coarse L is compressed using a rotary tablet press equipped with a 7/16" round, standard concave cup, plain, tooling. The cores were compressed at a theoretical weight of 555.6 mg and at a hardness of about 8–9 kg.

Next, the APAP tablet cores prepared above are coated with the controlled release coating of the present invention as follows. Methocel E5 premium is dispersed in three times its weight of hot purified water using a mixer. Thereafter, purified water at ambient temperature is added and mixed for approximately 1 hour. The mixture is allowed to cool. The amount of the ambient temperature purified water added is calculated such that the final coating suspension will have a concentration of about 20% of solids polymer and plasticizer.

In a separate container, triethyl citrate is mixed with Aquacoat ECD-30 for about 15 minutes. The Aquacoat/triethyl citrate suspension is then added to the methocel dispersion and mixed thoroughly. The appropriate quantity of APAP tablet cores are loaded into an Accella Cota coating pan. The Aquacoat/triethyl citrate coating suspension is sprayed from an appropriate spray gun until a weight gain of 10% per tablet is attained.

Further information concerning the controlled release coated APAP tablets is set forth in Table 53 below:

TABLE 53

| Ingredients | mg/tab |
| --- | --- |
| APAP IR tablet cores | 555.6 |
| Aquacoat ECD-30 (solids) | 27.78 |
| Methocel E5 premium | 27.78 |
| Triethyl Citrate | 11.11 |
| Purified water qs | |
| Total: | 622.27 |

After completion of the coating process, the coated tablets are discharged into a curing tray and cured in a temperature/humidity chamber at 60° C./80% RH for 72 hours in order to obtain a stabilized controlled release formulation. In vitro dissolution is carried out in a simulated intestinal fluid at 37° C. using the USP basket method at 100 RPM. The results are set forth in Table 54 below:

TABLE 54

| Hour | % APAP Dissolved |
| --- | --- |
| 1 | 2.7 |
| 2 | 6.3 |
| 4 | 13.9 |
| 8 | 27.1 |
| 12 | 36.4 |
| 18 | 47.7 |
| 24 | 58.4 |

EXAMPLE 27

In Example 27, controlled release APAP tablets having a slower dissolution than those of Example 26 are prepared.

First, immediate release APAP tablet cores are prepared in accordance with Example 26. Thereafter, APAP controlled release tablets are manufactured by coating the immediate release APAP tablet cores with a controlled release coating obtained from an aqueous dispersion of ethylcellulose containing 50% HPMC as a pore former to a 15% weight gain. The formula for the coated APAP tablet cores is set forth in Table 55 below:

TABLE 55

| Ingredients | mg/tab |
| --- | --- |
| APAP IR tablet cores | 555.6 |
| Aquacoat ECD-30 (solids) | 41.67 |
| Methocel E5 premium | 41.67 |
| Triethyl Citrate | 16.67 |
| Purified water qs | |
| Total: | 655.61 |

The method of manufacture of the coating suspension and its application to the cores are the same as set forth in Example 26. The coating suspension is applied until the requisite weight gain per tablet is attained. Thereafter, the coated tablets are cured in accordance with the procedures set forth with regard to Example 26. Next, in-vitro dissolution of the cured coated APAP controlled release formulation is carried out in the same manner as in Example 26. The results are set forth in Table 56 below:

TABLE 56

| Hour | % APAP Dissolved |
| --- | --- |
| 1 | 2.3 |
| 2 | 5.3 |
| 4 | 10.6 |
| 8 | 20.1 |
| 12 | 28.6 |
| 18 | 39.5 |
| 24 | 50 |

EXAMPLE 28

In Example 28, the release rate of the controlled release APAP tablet formulation of Example 26 is increased by increasing the quantity of the pore former. In this Example, immediate release APAP tablet cores are prepared according to the manufacturing procedure set forth in Example 26. Thereafter, a controlled release coating comprising an aqueous dispersion of ethylcellulose containing 60% HPMC as a pore former is applied to the immediate release APAP tablet cores.

Thereafter, the coating suspension is applied to the tablet cores in the manner set forth with regard to Example 26. The coating suspension is applied until the requisite weight gain per tablet is attained. Further information concerning the formulation of Example 28 is set forth in Table 57 below:

TABLE 57

| Ingredients | mg/tab |
| --- | --- |
| APAP IR tablet cores | 555.6 |
| Aquacoat ECD-30 (solids) | 22.224 |
| Methocel E5 premium | 33.336 |
| Triethyl Citrate | 11.112 |
| Purified water qs | |
| Total: | 622.272 |

Thereafter, the tablets of Example 28 are cured in the same manner as those of Example 26. In-vitro dissolution of the cured, coated tablets of Example 28 is set forth in Table 58 below:

TABLE 58

| Hour | % APAP Dissolved |
|---|---|
| 1 | 3.1 |
| 2 | 22.4 |
| 4 | 79.4 |
| 8 | 100.1 |

EXAMPLE 29

In Example 29, the dissolution rate of the tablets of Example is increased by virtue of increasing the amount of pore former contained in the controlled release coating to 70%.

In Example 29, immediate release tablet cores are prepared in accordance with the procedure set forth with regard to Example 26. Thereafter, the immediate release cores are coated with a controlled release coating comprising an aqueous dispersion of ethylcellulose containing 70% HPMC as the pore former. The coating is contained until a weight gain of 10% is achieved. The formula for the coated APAP tablet cores is set forth in Table 59 below:

TABLE 59

| Ingredients | mg/tab |
|---|---|
| APAP IR tablet cores | 555.6 |
| Aquacoat ECD-30 (solids) | 16.668 |
| Methocel E5 premium | 38.892 |
| Triethyl Citrate | 11.112 |
| Purified water qs | |
| Total: | 622.272 |

Thereafter, the coated tablets are cured under the same conditions set forth in Example 26. In vitro dissolution is then carried out as set forth in Example 26. The results are set forth in Table 60 below:

TABLE 60

| Hour | % APAP Dissolved |
|---|---|
| 1 | 97.2 |
| 2 | 102.8 |

The examples provided above are not meant to be exclusive. Many other variations of the present invention would be obvious to those skilled in the art.

What is claimed is:

1. A controlled release formulation comprising a substrate containing an active agent in an amount sufficient to provide an effect in an environment of use, said substrate coated with an aqueous dispersion of plasticized ethylcellulose in an amount sufficient to obtain a controlled release of said active agent when said formulation is exposed to an environmental fluid, said coated substrate being cured at a temperature greater than the glass transition temperature of the aqueous dispersion of plasticized ethylcellulose and at a relative humidity from about 60% to about 100% for a sufficient period of time until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions of at least one month at a temperature of 37° C. and at a relative humidity of 80%.

2. The formulation of claim 1, wherein said substrate is coated to a weight gain from about 2 to about 30%.

3. The formulation of claim 1, wherein said active agent is selected from the group consisting of a systemically active therapeutic agent, a locally active therapeutic agent, a disinfecting agent, a cleansing agent, a fragrance, a fertilizing agent, a deodorant, a dye, an animal repellant, an insect repellant, a pesticide, a herbicide, a fungicide, and a plant growth stimulant.

4. The formulation of claim 3, wherein said locally active therapeutic agent is selected from the group consisting of an antibiotic, a breath freshener, an antitussive agent, an analgesic, a local anesthetic, an antiseptic, an anti-inflammatory agent, a hormonal agent, and an acidity reducing agent.

5. The formulation of claim 3, wherein said systemically active therapeutic agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

6. The formulation of claim 5, wherein said active agent is an opioid analgesic selected from the group consisting of hydromorphone, oxycodone, morphine, levorphanol, methadone, meperidine, heroin, dihydrocodeine, codeine, dihydromorphine, buprenorphine, salts of any of the foregoing, and mixtures of any of the foregoing.

7. The formulation of claim 1, wherein said substrate is a pharmaceutically acceptable bead, and a plurality of said coated, cured beads are placed in a capsule in an amount sufficient to provide an effective controlled release dose when contacted by an aqueous solution.

8. The formulation of claim 1, wherein said substrate is a tablet core.

9. The formulation of claim 7, wherein said beads are coated with said aqueous dispersion of ethylcellulose to a weight gain from about 2 to about 25 percent.

10. The formulation of claim 9, wherein said coating is cured for a time period from about 48 to about 72 hours, until said endpoint is reached.

11. The formulation of claim 10, wherein said coating is cured at a relative humidity of about 85%.

12. The formulation of claim 1, wherein said coating further comprises a release-modifying agent in an amount effective to modify the rate of release of said active agent from said cured, coated substrate.

13. The formulation of claim 12, wherein said release-modifying agent is selected from the group consisting of a hydrophilic polymer, a semi-permeable polymer, an erosion-promoting polymer, an agent capable of making microporous lamina, a pore-former and mixtures of any of the foregoing.

14. The formulation of claim 12, wherein said coating comprises from about 0.1% to about 70% of said release-modifying agent.

15. The formulation of claim 12, wherein said coating comprises from about 0.1% to about 50% of said release-modifying agent.

16. The formulation of claim 12., wherein said coating comprises from about 0.1% to about 25% of said release-modifying agent.

17. The formulation of claim 12, wherein said release-modifying agent is selected from the group consisting of hydroxypropylmethylcellulose, lactose, metal stearates and mixtures of any of the foregoing.

18. The formulation of claim 1, which provides a stabilized dissolution of said active agent which is unchanged after exposure to accelerated storage conditions of a temperature of 40° C. and a relative humidity of 75% for 3 months.

19. The formulation of claim 1, which provides a stabilized dissolution of said active agent which is unchanged after exposure to accelerated storage conditions which are deemed appropriate by the United States Food & Drug Administration for the purpose of according expiration dating for said formulation.

20. The formulation of claim 17, wherein said cured coated substrate, when subjected to in-vitro dissolution after exposure to said accelerated conditions, releases an amount of said active agent which does not vary at any given time point by more than about 20% of the total amount of active agent released when compared to in-vitro dissolution conducted prior to storage.

21. The formulation of claim 1, wherein a portion of the amount of said active agent included in said formulation is incorporated into a coating on said substrate.

22. A method for obtaining an controlled release formulation of an active agent, comprising:

preparing a solid substrate comprising an active agent;

coating said substrate with a sufficient amount an aqueous dispersion of plasticized ethylcellulose to obtain a predetermined controlled release of said active agent when said coated substrate is exposed to an environmental fluid, and curing said coated substrate at a temperature greater than the glass transition temperature of the aqueous dispersion of plasticized ethylcellulose and at a relative humidity from about 60% to about 100% until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions of at least one month at a temperature of 37° C. and at a relative humidity of 80%.

23. The method of claim 22, further comprising preparing said substrate for oral administration by coating said therapeutically active agent onto the surface of pharmaceutically acceptable beads, and preparing an oral dosage form by placing a sufficient quantity of cured coated beads into a capsule.

24. The method of claim 22, further comprising preparing said substrate for oral administration by incorporating said therapeutically active agent into a tablet.

25. The method of claim 22, further comprising coating said substrate comprising said therapeutically active agent with a barrier agent prior to overcoating with said aqueous dispersion of ethylcellulose.

26. The method of claim 25, wherein said barrier agent comprises hydroxypropylmethylcellulose.

27. The method of claim 22, wherein said coated particles are cured for about 48 to about 72 hours, until said endpoint is reached.

28. The method of claim 22, further comprising coating said substrate to a weight gain from about 2 to about 25%.

29. The method of claim 22, wherein said active agent is selected from the group consisting of a systemically active therapeutic agent, a locally active therapeutic agent, a disinfecting agent, a cleansing agent, a fragrance, a fertilizing agent, a deodorant, a dye, an animal repellant, an insect repellant, a pesticide, a herbicide, a fungicide, and a plant growth stimulant.

30. The method of claim 22, wherein said locally active therapeutic agent is selected from the group consisting of an antibiotic, a breath freshener, an antitussive agent, an analgesic agent, a local anesthetic, an antiseptic, an anti-inflammatory agent, a hormonal agent, and an acidity-reducing agent.

31. The method of claim 22, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

32. The method of claim 22, wherein said active agent is an opioid analgesic selected from the group consisting of hydromorphone, oxycodone, morphine, levorphanol, methadone, meperidine, heroin, dihydrocodeine, codeine, dihydromorphine, buprenorphine, salts of any of the foregoing, and mixtures of any of the foregoing.

33. The method of claim 27, wherein said coating is cured at a relative humidity of about 85%.

34. The method of claim 22, wherein said coating further comprises a release-modifying agent in an amount effective to modify the rate of release of said active agent from said cured, coated substrate.

35. The method of claim 22, wherein said release-modifying agent is selected from the group consisting of a hydrophilic polymer, a semi-permeable polymer, an erosion-promoting polymer, an agent capable of making microporous lamina, a pore-former, and mixtures of any of the foregoing.

36. The method of claim 22, wherein said coating comprises from about 0.1% to about 70% of said release-modifying agent.

37. The method of claim 22, wherein said coating comprises from about 0.1% to about 50% of said release-modifying agent.

38. The method of claim 22, wherein said coating comprises from about 0.1% to about 25% of said release-modifying agent.

39. The method of claim 22, wherein said release-modifying agent is selected from the group consisting of hydroxypropylmethylcellulose, lactose, metal stearates, and mixtures of any of the foregoing.

40. A solid controlled release formulation, comprising a substrate containing an active agent in an amount sufficient to provide an effect in an environment of use, said substrate coated with an aqueous dispersion of plasticized ethylcellulose in an amount sufficient to obtain a controlled release of said active agent when said formulation is exposed to an environmental fluid, said coated substrate being cured at a temperature greater than the glass transition temperature of the aqueous dispersion of plasticized ethylcellulose and at a relative humidity from about 60% to about 100% to cause individual ethylcellulose particles in said coating to coalesce and to gradually slow the release of said active agent when exposed to an environmental fluid, until an endpoint is reached at which said cured coated substrate, when subjected to in-vitro dissolution, releases said active agent in amounts which do not vary at any time point along the dissolution curve by more than about 20% of the total amount of active agent released, when compared to the in-vitro dissolution of said coated substrate prior to curing.

41. The formulation of claim 40, wherein said cured, coated substrate provides the same rate of release immediately after curing to said endpoint, and after subsequent exposure to accelerated storage conditions of one month at a temperature of 37° C. and at a relative humidity of 80%.

42. The formulation of claim 40, wherein said cured, coated substrate provides the same rate of release immediately after curing to said endpoint, and after subsequent exposure to accelerated storage conditions of one month at a temperature of 40° C. and at a relative humidity of 75%.

43. The formulation of claim 40, wherein said substrate is coated to a weight gain from about 2% to about 25%.

44. The formulation of claim 40, wherein said active agent is selected from the group consisting of a systemically active therapeutic agent, a locally active therapeutic agent, a disinfecting agent, a cleansing agent, a fragrance, a fertilizing agent, a deodorant, a dye, an animal repellant, an insect repellant, a pesticide, a herbicide, a fungicide, and a plant growth stimulant.

45. The formulation of claim 40, wherein said locally active therapeutic agent is selected from the group consisting of an antibiotic, a breath freshener, an antitussive agent, an analgesic agent, a local anesthetic, an antiseptic, an anti-inflammatory agent, a hormonal agent, and an acidity reducing agent.

46. The formulation of claim 44, wherein said systemically active therapeutic agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

47. The formulation of claim 40, wherein said substrate is a pharmaceutically acceptable bead, and a plurality of said coated, cured beads are placed in a capsule in an amount sufficient to provide an effective controlled release dose when contacted by an aqueous solution.

48. The formulation of claim 40, wherein said substrate is a tablet core.

49. The formulation of claim 46, wherein said substrate is selected from the group consisting of a tablet core and a plurality of pharmaceutically inert beads, and said cured, coated formulation when administered orally provides effective blood levels of said systemically active therapeutic agent for about 24 hours.

50. The formulation of claim 49, wherein said systemically active therapeutic agent is an opioid analgesic selected from the group consisting of hydromorphone, oxycodone, morphine, levorphanol, methadone, meperidine, heroin, dihydrocodeine, codeine, dihydromorphine, buprenorphine, salts of any of the foregoing, and mixtures of any of the foregoing.

51. The formulation of claim 50, wherein said coating is cured for a time period from about 48 to about 72 hours, until said endpoint is reached.

52. The formulation of claim 51, wherein said coating is cured at a relative humidity of about 85%.

53. The formulation of claim 40, wherein said coating further comprises a release-modifying agent in an amount effective to modify the rate of release of said active agent from said cured, coated substrate.

54. The formulation of claim 53, wherein said release-modifying agent is selected from the group consisting of a hydrophilic polymer, a semi-permeable polymer, an erosion-promoting polymer, an agent capable of making microporous lamina, a pore-former, and mixtures of any of the foregoing.

55. The formulation of claim 54, wherein said coating comprises from about 0.1% to about 70% of said release-modifying agent.

56. The formulation of claim 54, wherein said coating comprises from about 0.1% to about 50% of said release-modifying agent.

57. The formulation of claim 54, wherein said coating comprises from about 0.1% to about 25% of said release-modifying agent.

58. The formulation of claim 40, wherein said coated substrate includes at least one passageway through said coating which modifies the release of said systemically active therapeutic agent.

59. The formulation of claim 55, wherein said release-modifying agent comprises hydroxypropylmethylcellulose.

60. A solid controlled release oral dosage formulation, comprising a substrate containing a systemically active therapeutic agent in an amount sufficient to provide a therapeutic effect when said formulation is orally administered, said substrate being coated with a cured aqueous dispersion of plasticized ethylcellulose to a weight gain from about 2% to about 25%, said coated substrate being cured at a temperature greater than the glass transition temperature of the aqueous dispersion of plasticized ethylcellulose and at a relative humidity from about 60% to about 100% for a sufficient period of time until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions of at least one month at a temperature of 37° C. and at a relative humidity of 80% and said coating being sufficient to obtain a controlled release of said active agent when measured by the USP Paddle Method at 100 rpm at 900 ml aqueous buffer (pH between 1.6 and 7.2) at 37° C. from about 12.5% to about 42.5% (by wt) active agent released after 1 hour, from about 25% to about 55% (by wt) active agent released after 2 hours, from about 45% to about 75% (by wt) active agent released after 4 hours and from about 55% to about 85% (by wt) active agent released after 8 hours, said coated substrate, when subjected to accelerated storage conditions of at least one month at 40° C./75% RH, releasing an amount of said therapeutically active agent upon in-vitro dissolution which does not vary at any given time point by more than about 20% of the total amount of therapeutically active agent released when compared to in-vitro dissolution conducted prior to storage.

61. The formulation of claim 60, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

62. The formulation of claim 61, wherein said active agent is an opioid analgesic selected from the group consisting of hydromorphone, oxycodone, morphine, levorphanol, methadone, meperidine, heroin, dihydrocodeine, codeine, dihydromorphine, buprenorphine, salts thereof, and mixtures thereof.

63. The formulation of claim 61, wherein said substrate is selected from the group consisting of a tablet core and a pharmaceutically acceptable bead, and a plurality of said coated, cured beads are placed in a capsule in an amount sufficient to provide an effective controlled release dose when said capsule is orally administered.

64. The formulation of claim 62, which is a once-a-day formulation.

65. The formulation of claim 61, wherein said coating further comprises a release-modifying agent in an amount effective to modify the rate of release of said active agent from said cured, coated substrate.

66. The formulation of claim 61, wherein said release-modifying agent is selected from the group consisting of a hydrophilic polymer, a semi-permeable polymer, an erosion-promoting polymer, an agent capable of making microporous lamina, a pore-former and mixtures of any of the foregoing.

67. The formulation of claim 60, wherein said coating comprises from about 0.1% to about 70% of said release-modifying agent.

68. The formulation of claim 60, wherein said coating comprises from about 0.1% to about 50% of said release-modifying agent.

69. The formulation of claim 60, wherein said coating comprises from about 0.1% to about 25% of said release-modifying agent.

70. The formulation of claim 61, wherein said release-modifying agent comprises up to about 10% of said coating, by weight.

71. The formulation of claim 60, wherein said coated substrate includes at least one passageway through said coating which modifies the release of said systemically active therapeutic agent.

72. The formulation of claim 60, wherein said release-modifying agent is selected from the group consisting of hydroxypropylmethylcellulose, lactose, metal stearates, and mixtures of any of the foregoing.

73. The formulation of claim 60, which provides a stabilized dissolution of said active agent which is unchanged after exposure to accelerated storage conditions of a temperature of 40° C. and a relative humidity of 75% for 3 months.

74. The formulation of claim 60, which provides a stabilized dissolution of said active agent which is unchanged after exposure to accelerated storage conditions which are deemed appropriate by the United States Food & Drug Administration for the purpose of according expiration dating for said formulation.

75. The formulation of claim 60, wherein a portion of the amount of said active agent included in said formulation is incorporated into a coating on said substrate.

76. The formulation of claim 60, which provides therapeutically effective blood levels of said systemically active therapeutic agent when administered orally for about 12 hours.

77. The formulation of claim 60, which provides therapeutically effective blood levels of said systemically active therapeutic agent when administered orally for about 24 hours.

78. The formulation of claim 62, which provides therapeutically effective blood levels of said opioid analgesic when administered orally for about 24 hours.

79. A method of treating a patient with a controlled release oral solid dosage form which provides an effective blood level of a therapeutically active agent for a predetermined amount of time, comprising:

preparing a solid substrate comprising a sufficient amount of a therapeutically active agent to provide therapeutically effective blood levels in the patient for about 12 to about 24 hours, coating said substrate with a sufficient amount an aqueous dispersion of plasticized ethylcellulose to obtain a predetermined controlled release of said active agent when said coated substrate is exposed to an environmental fluid, and curing said coated substrate at a temperature greater than the glass transition temperature of the aqueous dispersion of plasticized ethylcellulose and at a relative humidity from about 60% to about 100% until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions of at least one month at a temperature of 37° C. and at a relative humidity of 80%, and administering an oral solid dosage form comprising said cured, coated substrate to the patient to thereby obtain the desired therapeutic effect for about 12 to about 24 hours.

80. The method of claim 79, wherein said coated substrate is cured at a temperature greater than the glass transition temperature of the aqueous dispersion of plasticized ethylcellulose and at a relative humidity from about 60% to about 100%.

81. The method of claim 80, wherein said substrate comprises pharmaceutically acceptable inert beads, further comprising coating said therapeutically active agent onto the surface of said inert beads, and preparing said oral dosage form by placing a sufficient quantity of cured coated beads into a capsule.

82. The method of claim 79, further comprising preparing said substrate for oral administration by incorporating said therapeutically active agent into a tablet.

83. The method of claim 81, wherein said coated substrate is cured for about 48 to about 72 hours, until said endpoint is reached.

84. The method of claim 79, further comprising coating said substrate to a weight gain from about 2% to about 25%.

85. The method of claim 79, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

86. The method of claim 79, wherein said active agent is an opioid analgesic selected from the group consisting of hydromorphone, oxycodone, morphine, levorphanol, methadone, meperidine, heroin, dihydrocodeine, codeine, dihydromorphine, buprenorphine, salts thereof, and mixtures thereof.

87. The method of claim 85, wherein said oral solid dosage form provides a desired therapeutic effect for about 24 hours.

88. The method of claim 86, wherein said oral solid dosage form provides a desired therapeutic effect for about 24 hours.

89. The method of claim 79, further comprising incorporating a release-modifying agent in said aqueous dispersion of ethylcellulose in an amount effective to modify the rate of release of said active agent from said cured, coated substrate.

90. The method of claim 89, wherein said release-modifying agent is selected from the group consisting of a hydrophilic polymer, a semi-permeable polymer, an erosion-promoting polymer, an agent capable of making microporous lamina, a pore-former, and mixtures of any of the foregoing.

91. The method of claim 89, wherein said release-modifying agent is selected from the group consisting of hydroxypropylmethylcellulose, lactose, metal stearates, and mixtures of any of the foregoing.

92. An oral solid dosage form comprising:
a solid substrate comprising an effective amount of a therapeutically active agent,
a coating covering said substrate, said coating comprising a cured aqueous dispersion of ethylcellulose in an amount required to provide effective blood levels of said therapeutically active agent for at least about 12 hours, said coated substrate being cured at a temperature greater than the glass transition temperature of the aqueous dispersion of plasticized ethylcellulose and at a relative humidity from about 60% to about 100% for a sufficient period of time until a curing endpoint is reached at which said coated substrate provides a stabilized dissolution of said active agent which is unchanged after exposure to accelerated storage conditions, said endpoint being determined by comparing the dissolution profile of the formulation immediately after curing to the dissolution profile of the formulation after exposure to accelerated storage conditions of at least one month at a temperature of 37° C. and at a relative humidity of 80% and said coated substrate upon in-vitro dissolution testing providing a band range, when comparing the dissolution profile after exposure to accelerated storage conditions of at least one month at a temperature of 40° C. and a relative humidity of 75% to the dissolution profile prior to exposure to said accelerated conditions, which is not wider than about 20% of total active agent released at any point of time.

93. The oral solid dosage form of claim 92, wherein said coating further comprises from about 0.1% to about 70% by weight of a release-modifying agent.

94. The oral solid dosage form of claim 92, wherein said coating includes at least one passageway running from an exterior surface of said coating to said solid substrate, said passageway causing a desired modification of the release rate of said therapeutically active agent when said oral solid dosage form is exposed to aqueous fluids or gastrointestinal fluid.

95. The oral solid dosage form of claim 92, wherein the band range, when comparing the dissolution profile after exposure to accelerated storage conditions of at least one month at a temperature of 40° C. and a relative humidity of 75% to the dissolution profile prior to exposure to said accelerated conditions, does not differ by more than about 15%.

96. The oral solid dosage form of claim 92, wherein the band range, when comparing the dissolution profile after exposure to accelerated storage conditions of at least one month at a temperature of 40° C. and a relative humidity of 75% to the dissolution profile prior to exposure to said accelerated conditions, does not differ by more than about 10%.

97. The oral solid dosage form of claim 92 which provides effective blood levels of said therapeutically active agent for about 24 hours.

98. The dosage form of claim 92, wherein said substrate comprises a pharmaceutically acceptable inert bead upon which said therapeutically active agent is coated and a plurality of said coated beads are placed in a capsule to provide said effective amount of said therapeutically active agent.

99. The oral solid dosage form of claim 92 which is a coated tablet.

100. The controlled release dosage form of claim 93, wherein said release-modifying agent is selected from the group consisting of a hydrophilic polymer, a semi-permeable polymer, an erosion-promoting polymer, an agent capable of making microporous lamina, a pore-former, and mixtures of any of the foregoing.

101. A controlled release dosage form, comprising
a solid substrate comprising an effective amount of a therapeutically active agent, said solid substrate being coated with a cured aqueous dispersion of ethylcellulose in an amount effective to provide a controlled release of said therapeutically active agent when said coated substrate is exposed to gastrointestinal fluid, said coated substrate when subjected to invitro dissolution after exposure to accelerated storage conditions of at least one month at 40° C./75% RH releasing an amount of said therapeutically active agent which does not vary at any given dissolution time point by more than about 20% of the total amount of therapeutically active agent released when compared to in-vitro dissolution conducted prior to storage, said coated substrate being cured at a temperature greater than the glass transition temperature of the aqueous dispersion of plasticized ethylcellulose and at a relative humidity from about 60% to about 100% for about 48 to about 72 hours.

102. The controlled release dosage form of claim 101 which is administered once a day.

103. The controlled release dosage form of claim 101 which is administered twice a day.

104. The controlled release dosage form of claim 101 wherein said substrate comprises a pharmaceutically acceptable inert bead upon which said therapeutically active agent is coated and a plurality of said coated beads are placed in a capsule to provide said effective amount of said therapeutically active agent.

105. The controlled release dosage form of claim 101 which is a coated tablet.

106. The controlled release dosage form of claim 101, wherein said coating further comprises a release-modifying agent in an amount effective to modify the rate of release of said therapeutically active agent from said coated substrate.

107. The controlled release dosage form of claim 101, wherein said substrate is coated with said aqueous dispersion of ethylcellulose to a weight gain from about 2 to about 25%.

108. The controlled release dosage form of claim 102, wherein said therapeutically active agent is an opioid analgesic selected from the group consisting of hydromorphone, oxycodone, morphine, levorphanol, methadone, meperidine, heroin, dihydrocodeine, codeine, dihydromorphine, buprenorphine, salts thereof, and mixtures thereof.

109. The formulation of claim 40, wherein said cured coated substrate, when subjected to in-vitro dissolution, releases said active agent in amounts which do not vary at any time point along the dissolution curve by more than about 15% of the total amount of active agent released, when compared to the in-vitro dissolution of said coated substrate prior to curing.

110. The formulation of claim 40, wherein said cured coated substrate, when subjected to in-vitro dissolution, releases said active agent in amounts which do not vary at any time point along the dissolution curve by more than about 10% of the total amount of active agent released, when compared to the in-vitro dissolution of said coated substrate prior to curing.

111. A method of treating a human patient, comprising orally administering the oral solid dosage form of claim 92.

112. A method of treating a human patient, comprising orally administering the controlled release dosage form of claim 101.

113. A method of treating a human patient, comprising orally administering the solid controlled release oral dosage formulation of claim 60.

114. A method of treating a human patient, comprising orally administering the solid controlled release formulation of claim 40.

115. A method of treating a human patient, comprising orally administering the formulation of claim 5.

116. The formulation of claim 3, wherein said locally active therapeutic agent is selected from the group consisting of an antiviral agent, an antifungal agent, an antiplaque agent, an anti-cariogenic agent, and a tooth desensitizer.

117. The method of claim 22, wherein said locally active therapeutic agent is selected from the group consisting of an antiviral agent, an antifungal agent, an antiplaque agent, an anticariogenic agent, and a tooth desensitizer.

118. The formulation of claim 40, wherein said locally active therapeutic agent is selected from the group consisting of an antiviral agent, an antifungal agent, an antiplaque agent, an anti-cariogenic agent, and a tooth desensitizer.

* * * * *